United States Patent
Landry et al.

(10) Patent No.: US 9,314,341 B2
(45) Date of Patent: Apr. 19, 2016

(54) SURGICAL METHODS AND INSTRUMENTS FOR IMPLANTING A JOINT UNLOADING SYSTEM

(75) Inventors: Michael E. Landry, Austin, TX (US); Mary O'Connell, Menlo Park, CA (US); Anton G. Clifford, Mountain View, CA (US); Alan C. Regala, Seattle, WA (US)

(73) Assignee: MOXIMED, INC., Hayward, CA (US)

( * ) Notice: Subject to any disclaimer, the term of this patent is extended or adjusted under 35 U.S.C. 154(b) by 611 days.

(21) Appl. No.: 13/564,095

(22) Filed: Aug. 1, 2012

(65) Prior Publication Data

US 2013/0138218 A1 May 30, 2013

Related U.S. Application Data

(63) Continuation-in-part of application No. 12/915,606, filed on Oct. 29, 2010, now abandoned.

(51) Int. Cl.
*A61F 2/08* (2006.01)
*A61F 2/38* (2006.01)
(Continued)

(52) U.S. Cl.
CPC . *A61F 2/38* (2013.01); *A61B 17/56* (2013.01); *A61B 17/8872* (2013.01); *A61F 2/0811* (2013.01); *A61B 17/1764* (2013.01); *A61B 17/808* (2013.01); *A61B 17/8061* (2013.01); *A61B 17/8897* (2013.01); *A61B 2017/567* (2013.01); *A61B 2019/461* (2013.01); *A61F 2/0805* (2013.01); *A61F 2/3836* (2013.01); *A61F 2002/0823* (2013.01); *A61F 2002/0864* (2013.01); *A61F 2002/0888* (2013.01);

(Continued)

(58) Field of Classification Search
CPC .............. A61B 17/68–17/688; A61B 17/56; A61B 17/8897
USPC .............. 623/13.11–13.19, 18.11, 20.1–20.1, 623/20.2–20.299
See application file for complete search history.

(56) References Cited

U.S. PATENT DOCUMENTS 5,928,234 A 7/1999 Manspeizer
6,656,189 B1 12/2003 Wilson et al.
(Continued)

FOREIGN PATENT DOCUMENTS

WO WO2012024306 2/2012

OTHER PUBLICATIONS

Office Action in co-pending U.S. Appl. No. 12/915,606 dated Apr. 10, 2014.
(Continued)

*Primary Examiner* — Matthew Lawson
(74) *Attorney, Agent, or Firm* — Adam J. Cermak; Cermak Nakajima & McGowan LLP

(57) ABSTRACT

Positioning instruments and related methods are described for implanting an joint unloading system for treating joints. The positioning instruments and methods allow the joint unloading system to be positioned at a joint such that the desired motion will occur for the particular design of a particular joint unloading system which is to be implanted. The positioning instruments include a locating instrument for locating an anatomical feature and a target location for implantation of the joint unloading system, a verification instrument for verification of the target location, an alignment guide, a placement guide for guiding placement of a part of the joint unloading system, and positioning device for aligning portions of the joint unloading system.

9 Claims, 27 Drawing Sheets

(51) Int. Cl.
 *A61B 17/56* (2006.01)
 *A61B 17/88* (2006.01)
 *A61B 17/80* (2006.01)
 *A61B 19/00* (2006.01)
 *A61F 2/30* (2006.01)
 *A61B 17/17* (2006.01)

(52) U.S. Cl.
 CPC . *A61F2002/30563* (2013.01); *A61F 2240/005* (2013.01); *A61F 2250/0006* (2013.01)

(56) References Cited

U.S. PATENT DOCUMENTS

| | | | |
|---|---|---|---|
| 7,294,133 | B2 | 11/2007 | Zink et al. |
| 2002/0151903 | A1 | 10/2002 | Takei et al. |
| 2005/0085920 | A1 | 4/2005 | Williamson |
| 2008/0262500 | A1 | 10/2008 | Collazo |
| 2009/0014016 | A1 | 1/2009 | Clifford et al. |
| 2009/0018656 | A1 | 1/2009 | Clifford et al. |
| 2009/0018665 | A1* | 1/2009 | Clifford et al. ............ 623/18.11 |
| 2009/0024131 | A1 | 1/2009 | Metzger et al. |
| 2009/0276054 | A1 | 11/2009 | Clifford et al. |
| 2010/0063549 | A1* | 3/2010 | Orbay et al. .................. 606/281 |
| 2010/0198275 | A1 | 8/2010 | Chana et al. |
| 2011/0112639 | A1 | 5/2011 | Regala et al. |

OTHER PUBLICATIONS

Office Action from U.S. Appl. No. 13/653,230 (Mar. 3, 2015).
Office Action from U.S. Appl. No. 13/653,221 (Mar. 6, 2015).
Office Action for co-pending U.S. Appl. No. 13/653,249 (Sep. 18, 2015).
Office Action for co-pending U.S. Appl. No. 13/653,230 (Nov. 12, 2015).

* cited by examiner

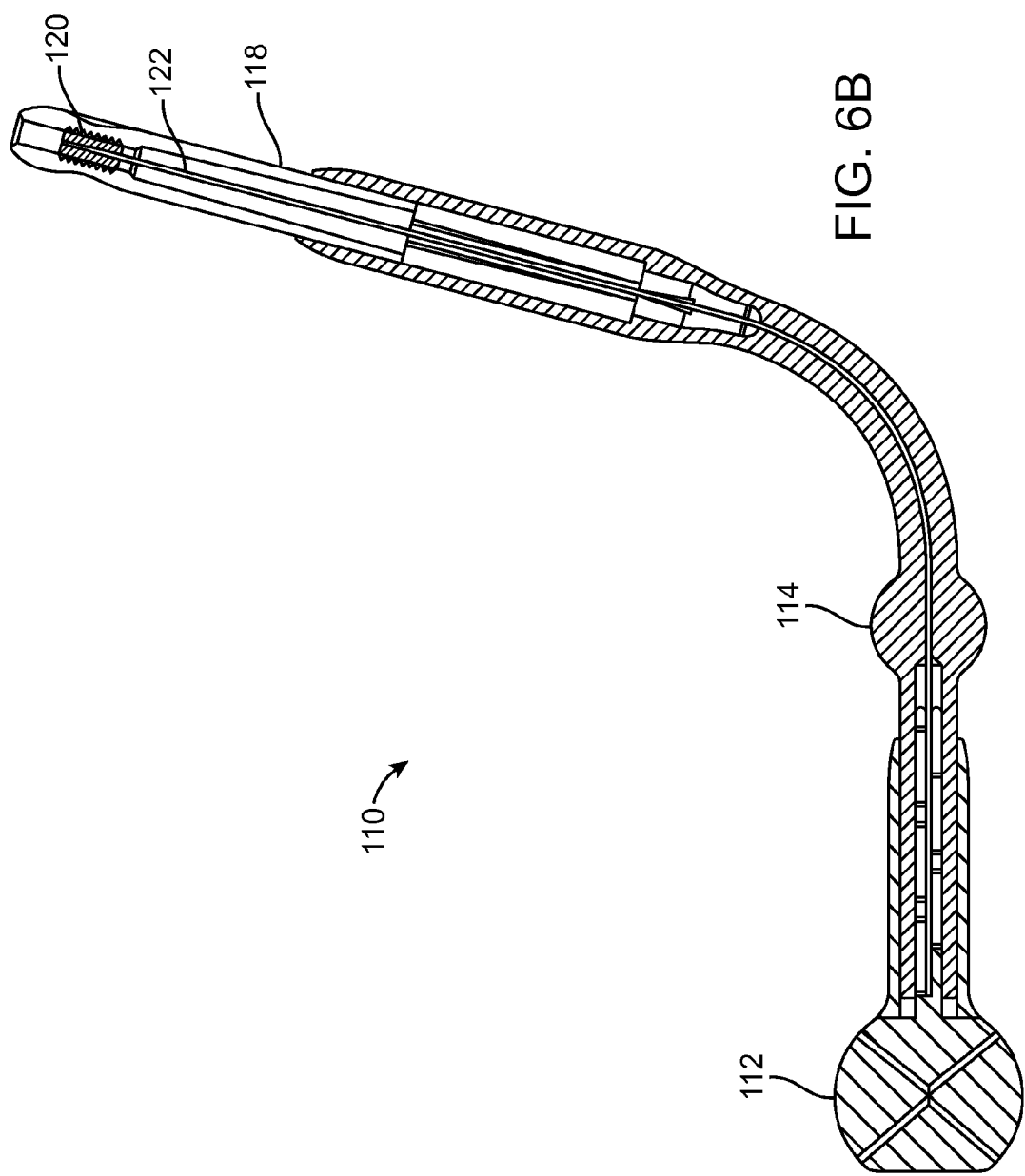

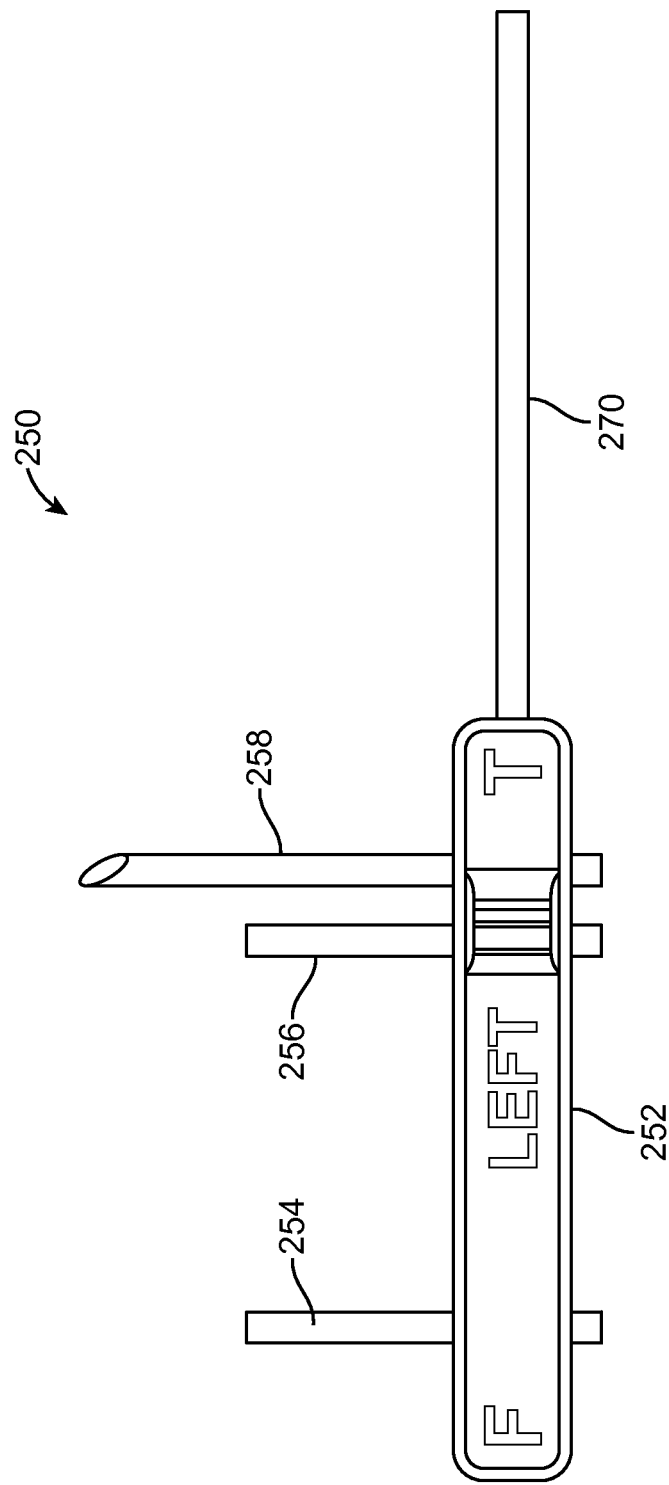

SURGICAL METHODS AND INSTRUMENTS FOR IMPLANTING A JOINT UNLOADING SYSTEM

CROSS REFERENCES TO RELATED APPLICATIONS

This application is a continuation-in-part of U.S. application Ser. No. 12/915,606, filed Oct. 29, 2010, the entire disclosure of which is expressly incorporated herein.

BACKGROUND

The present disclosure is directed towards positioning instruments and related methods for implanting a joint unloading system, and more particularly to tools and surgical procedures for implanting a joint unloading system.

Joint replacement is one of the most common and successful operations in modern orthopaedic surgery. It consists of replacing painful, arthritic, worn or diseased parts of a joint with artificial surfaces shaped in such a way as to allow joint movement. Osteoarthritis is a common diagnosis leading to joint replacement. Such procedures are a last resort treatment as they are highly invasive and require substantial periods of recovery and permanently alter the joint. Total joint replacement, also known as total joint arthroplasty, is a procedure in which all articular surfaces at a joint are replaced. This contrasts with hemiarthroplasty (half arthroplasty) in which only one bone's articular surface at a joint is replaced and unincompartmental arthroplasty in which the articular surfaces of only one of multiple compartments at a joint (such as the surfaces of the thigh and shin bones on just the inner side or just the outer side at the knee) are replaced.

Arthroplasty as a general term, is an orthopaedic procedure which surgically alters the natural joint in some way. This includes procedures in which the arthritic or dysfunctional joint surface is replaced with something else, and procedures which are undertaken to reshape or realign the joint by osteotomy or some other procedure. As with joint replacement, these other arthroplasty procedures are also highly invasive procedures characterized by relatively long recovery times. A previously popular form of arthroplasty was interpositional arthroplasty in which the joint was surgically altered by insertion of some other tissue like skin, muscle or tendon within the articular space to keep inflammatory surfaces apart. Another previously done arthroplasty was excisional arthroplasty in which articular surfaces were removed leaving scar tissue to fill in the gap. Among other types of arthroplasty are resection(al) arthroplasty, resurfacing arthroplasty, mold arthroplasty, cup arthroplasty, silicone replacement arthroplasty, and osteotomy to affect joint alignment or restore or modify joint congruity. When successful, arthroplasty results in new joint surfaces which serve the same function in the joint as did the surfaces that were removed. Any chondrocytes (cells that control the creation and maintenance of articular joint surfaces), however, are either removed as part of the arthroplasty, or left to contend with the resulting joint anatomy. Because of this, none of the therapies which remove the joint surfaces are chondro-protective.

A widely-applied type of osteotomy is one in which bones are surgically cut to improve alignment. A misalignment due to injury, bone abnormality or disease in a joint relative to the direction of load can result in an imbalance of forces and pain in the affected joint. The goal of osteotomy is to surgically re-align the bones at a joint and thereby relieve pain by shifting forces across the joint to less damaged joint surfaces. This can also increase the lifespan of the joint. When addressing osteoarthritis in the knee joint, this procedure involves surgical re-alignment of the joint by cutting and reattaching part of one of the bones at the knee to change the joint alignment, and this procedure is often used in younger, more active or heavier patients. Most often, high tibial osteotomy (HTO) (the surgical re-alignment of the upper end of the shin bone (tibia) to address knee malalignment) is the osteotomy procedure done to address osteoarthritis and it often results in a decrease in pain and improved function. However, HTO does not address ligamentous instability—only mechanical alignment. HTO is associated with good early results, but results deteriorate over time.

It has been found that excess loading of the joint is the primary contributing factor in the progression of osteoarthritis disease. It has also been shown that a decrease in load, such as by weight loss can result in decrease in disease progression and in pain relief.

Certain approaches to treating osteoarthritis contemplate external devices such as braces or fixators which attempt to control the motion of the bones at a joint or apply cross-loads at a joint to shift load from one side of the joint to the other. A number of these approaches have had some success in alleviating pain by reducing loads on diseased joints but have ultimately been unsuccessful due to lack of patient compliance or the inability of the devices to facilitate and support the natural motion and function of the diseased joint.

Certain prior approaches to treating osteoarthritis have also failed to account for all of the basic functions of the various structures of a joint in combination with its unique movement. In addition to addressing the loads and motions at a joint, an ultimately successful approach should both acknowledge the dampening and energy absorption functions of the anatomy, and be implantable via a minimally invasive technique. Device constructs which are relatively rigid do not allow substantial energy storage. For these relatively rigid constructs, energy is transferred rather than stored or absorbed relative to a joint. By contrast, the natural joint is a construct comprised of elements of different compliance characteristics such as bone, cartilage, synovial fluid, muscles, tendons, ligaments, etc. as described above. These dynamic elements include relatively compliant ones (ligaments, tendons, fluid, cartilage) which allow for substantial energy absorption and storage, and relatively stiffer ones (bone) that allow for efficient energy transfer. The cartilage in a joint compresses under applied force and the resultant force displacement product represents the energy absorbed by cartilage. The fluid content of cartilage also acts to stiffen its response to load applied quickly and dampen its response to loads applied slowly. In this way, cartilage acts to absorb and store, as well as to dissipate energy.

Approaches for surgically implanting extra-articular mechanical joint unloading apparatus or joint unloading systems have been developed. As precise and effective placement are important to the efficacy of an implanted extra-articular mechanical unloading apparatus, further advancements in patient preparation and device-to-anatomy juxapositional relationships have been found to be both useful and necessary.

With the foregoing applications in mind, it has been found to be necessary to develop effective systems and tools for mounting implantable joint unloading system to body anatomy.

For joint unloading systems to function optimally, they must be selected and positioned to unload the joint without overloading the implant. Therefore, what is needed is a refined surgical approach to implanting a device which complements underlying or adjacent anatomy. The present disclosure satisfies these and other needs.

SUMMARY OF THE DISCLOSURE

Briefly and in general terms, the present disclosure is directed towards treating diseased or mal-aligned body joints, typically affected by osteoarthritis, using a joint unloading system without limiting the range of motion of the patient's articulating joint. The positioning instruments and related methods are described herein for implanting such joint unloading system.

In one embodiment, a method of implanting a device at a joint includes the steps of inserting a first reference marker into a first bone of the joint, inserting a second reference marker into a second bone of the joint, connecting the first and second reference markers to a verification tool, moving the joint through a predetermined range of motion and utilizing the verification tool to determine whether the first and second reference markers move in a desired kinematic pattern with respect to one another throughout the predetermined range of motion, relocating one of the reference markers if the desired kinematic pattern is not achieved, and implanting the device across the joint.

In another embodiment, a verification tool for verification of a location for implantation of an extra-articular joint unloading device at a joint includes a tool body, a first connection member on the tool body, the first connection member configured to be connected to a first reference marker located in a first bone, the first connection member allowing rotation of the tool with respect to the first bone, a second connection member on the tool body, the second connection member configured to be connected to a second reference marker located in a second bone, the second connection member allowing rotation of the tool with respect to the second bone, wherein at least one of the first and second connection members is movable with respect to the tool body, and an indicator configured to provide a user with information about the location of at least one of the first and second reference markers as the joint is articulated.

In another embodiment, the verification tool can include a first snap-on connection to a first reference marker located on a first bone and a second snap-on connection to a second reference marker on a second bone. The tool further includes a handle having indicators for reflecting kinematic patterns of the reference markers as the joint is articulated. The handle is configured to extend out and away from an interventional site for convenient manipulation and reading of the indicators by an operator.

In one embodiment, an alignment guide for placing an joint unloading device at a joint includes a body configured to receive a plurality of reference markers inserted into bones on either side of a knee joint and an indicator rod extending longitudinally from the body, wherein the indicator rod is configured to be aligned with an axis of the tibia when the knee joint is placed in extension.

In another embodiment, a tool for selecting one base from among a plurality of bases having different base geometries for an implant at a joint includes, a tool body having a bone contacting surface shape generally corresponding to a bone contacting surface shape of the plurality of bases from which the one base is to be selected, a pointer rotatably connected to the trial base, an indicia and indicator arm portion rotatably connected to the trial base. When the trial base is positioned on a bone of the joint, the pointer is disposed in a position relative to the indicia that indicates a desired base contour to be selected.

In another embodiment of a selection tool, a femoral trial assembly can include a trial base which is rotatably connected to a pointer and an indicia and indication arm structure. The trial base is configured to be placed onto the femur and the indicator arm is alignable with a tibial reference marker. When so configured, the pointer identifies from the indicia the best angular contour for the femoral base. Various angles of contours are contemplated for the femoral base.

In a further embodiment, a system for selecting one base from among a plurality of bases having different base geometries for an implantable joint unloading system comprises an alignment guide comprising a body having at least one opening for receiving a first reference marker inserted into a femur and at least one opening for inserting a second reference marker into a tibia, and an indicator rod extending from the body, wherein the indicator rod is configured to be aligned with an axis of tibia when the knee joint is placed in extension; and a trial base having at least one opening configured to be received over the first reference marker, a pointer movably connected to the trial base, and an indicia and indicator arm portion rotatably connected to the trial base, wherein, when the trial base is positioned on a bone of the joint, the pointer is disposed in a position relative to the indicia that indicates a desired base to be selected.

In another embodiment, a method for selecting one base from among a plurality of bases having different base geometries for an implantable joint unloading system comprises the steps of inserting a first reference marker in the femur; connecting an alignment guide to the first reference marker with an indicator rod extending from the alignment guide aligned with an axis of tibia when the knee joint is placed in extension; inserting a second reference marker through an opening in the alignment guide and into the tibia; and positioning a trial base over the first reference marker, rotating the trial base until an arm of the trial base points to the second reference marker, and selecting a desired base to be implanted based on an indicia shown on the trial base.

Other features of the joint unloading system, instruments and methods will become apparent from the following detailed description, taken in conjunction with the accompanying drawings, which illustrate, by way of example, the principles of the embodiments.

BRIEF DESCRIPTION OF THE DRAWINGS

FIG. 6B is a cross-sectional view, depicting the verification tool of FIG. 6A;

FIGS. 8A-8C are perspective and side views of an alignment guide assembly;

DETAILED DESCRIPTION

Figure 1:
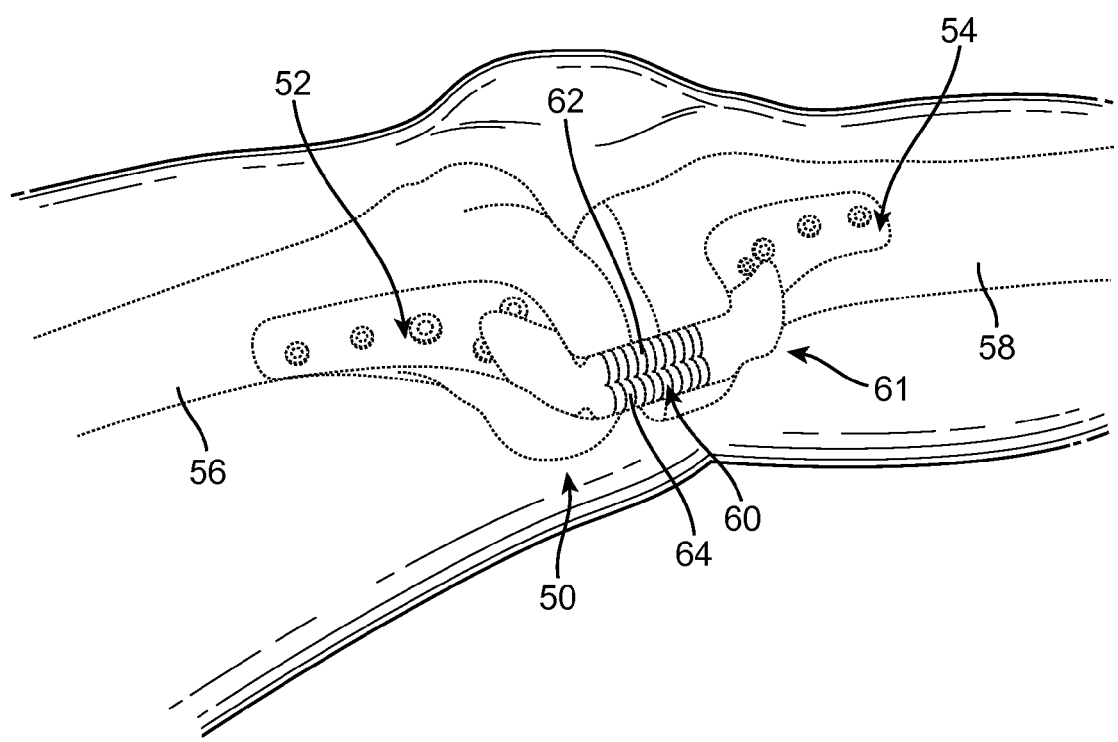
FIG. 1 is a perspective view, depicting an extra-articular implantable mechanical joint unloading system.

Referring now to the drawings, which are provided by way of example and not limitation, the present disclosure is directed towards apparatus for treating body tissues. In applications relating to the treatment of body joints, the described approach seeks to alleviate pain associated with the function of diseased or malaligned members forming a body joint. Whereas the present invention is particularly suited to address issues associated with osteoarthritis, the energy manipulation accomplished by the present invention lends itself well to broader applications. Moreover, the present invention is particularly suited to treating synovial joints such as the knee, finger, wrist, ankle and shoulder.

In one particular aspect, the presently disclosed joint unloading systems involve varying energy absorption and transfer during the rotation of a joint, such as a knee joint. FIG. 1 illustrates an implantable joint unloading system for absorption of forces normally transmitted through a joint in order to relieve pain, such as pain associated with osteoarthritis.

U.S. Patent Publication No. 2009/0014016, which is incorporated herein by reference in its entirety, describes certain embodiments of extra-articular energy absorbing systems. These energy absorbing systems include geometry which accomplishes variable energy absorption designed to minimize and complement the dampening effect and energy absorption provided by the anatomy of the body, such as that found at a body joint. It has been postulated that to minimize pain, in an osteoarthritic joint absorption of 1-40% of forces, in varying degrees, may be necessary. Variable absorption in the range of 5-20% can be a target for certain applications. In certain specific applications, temporary distraction (e.g., less than 3 months) is employed in the energy manipulation approach.

Referring now to FIG. 1, one embodiment of an joint unloading system 50 is shown affixed to a knee joint to absorb at least a portion of the energy normally transmitted by the knee anatomy. The joint unloading system 50 includes a proximal 52 base positioned on the femur 56 and a distal 54 base positioned on the tibia 58 of the typical knee joint. It is noted that portions of the base 52, 54 are contoured to match potential mounting surfaces of the femur and tibia 56, 58. Also shown is an energy absorbing or joint unloading device 60 that is located between and mounted to the bases 52, 54. In FIG. 1A, the joint unloading system 60 is shown with a sheath 61 which covers internal components, protects the moving elements from impingement by surrounding tissues and prevents the devices from damaging surrounding tissue. For viewing purposes the sheath 61 is omitted from FIG. 2.

The joint unloading system 50 as shown includes two springs 62, 64, however other numbers of springs may also be used. The joint unloading system 50 has the capacity to absorb energy in addition to transferring energy from the joint. FIG. 1 shows the knee joint at full extension. In the example of FIG. 1, maximum load is applied to the springs 62, 64 of the joint unloading device 50 at full extension during the stance phase of the gait cycle. When the knee joint is flexed to 90°, such as during the swing phase of the gait cycle or when the patient is seated, zero load is absorbed from the knee by the springs 62, 64. In this example, when the joint unloading device 50 is correctly positioned on the knee, the device is actively working in compression when the knee is at or near full extension. The joint unloading device 50 lengthens as the knee swings from full extension to flexion and subsequently shortens as the knee swings from flexion to full extension such that the springs begin to be compressed between the ends of the device to absorb at least a portion of the load that the knee articulating surfaces normally would experience.

The joint unloading device 50 and bases 52, 54 are mounted across the joint such that once the spring has achieved a predetermined amount of compression, and therefore load, the articulating surfaces of the knee then carry a portion of the load in combination with the joint unloading device such that the joint unloading device does not "bottom out".

Figure 2:
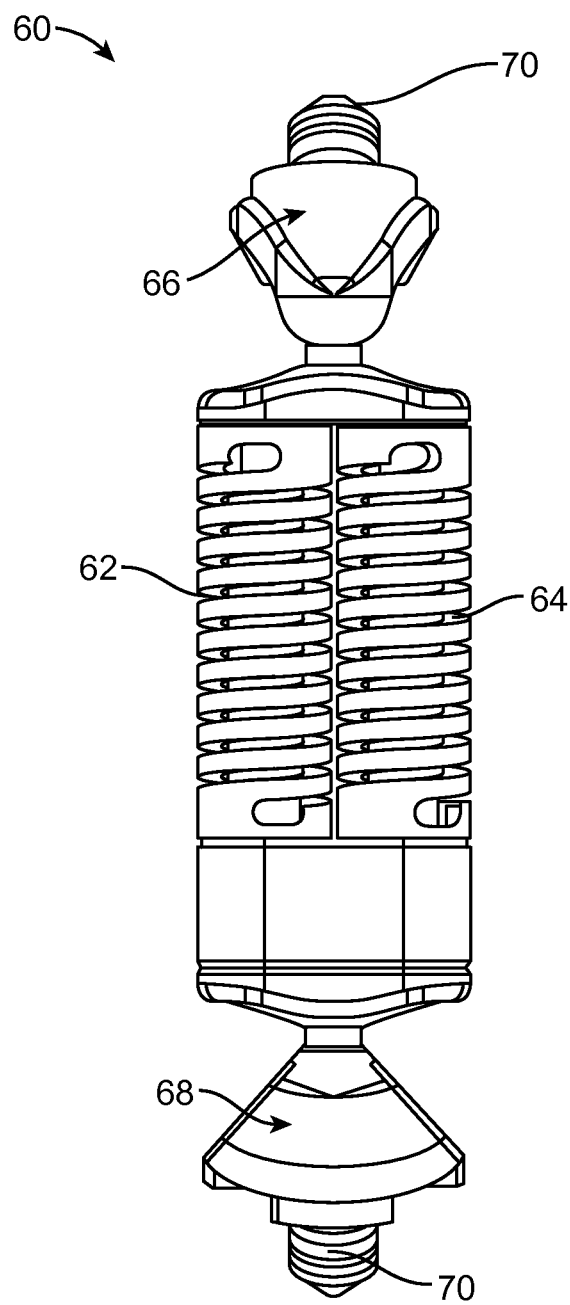
FIG. 2 is a side view, depicting the absorber of the system of FIG. 1 with the sheath removed.

Still referring to FIG. 1, as well as FIG. 2, one embodiment of an joint unloading device 60 includes two machined springs 62, 64. These springs 62, 64 are each positioned about guides (not shown) which support the springs allowing the springs to act in compression when the knee is in extension or at low flexion angles and support the springs in an unloaded position when the knee is at higher flexion angles. The guides about which the springs 62, 64 are located may be in the form of telescoping members, such as a piston and barrel which allow the opposite ends of the joint unloading device 60 to move in a linear path toward and away from each other. The joint unloading device also includes a proximal (femoral) end 66 and a distal (tibial) end 68 which are connectable to the bases 52, 54 by a known connection mechanism 70, such as a taper lock.

The joint unloading device 60, as illustrated, also includes two ball and socket joints within the proximal and distal ends 66, 68 which allow anterior/posterior, medial/lateral, and axial rotation of the joint unloading device 60 with respect to the bases 52, 54. The range of motion of the components of the system can be determined by the bearing/socket geometry, base/absorber geometry and relative position of the base to absorber at final implantation. Identical ball/sockets arrangements can be provided on both sides of a knee joint but different arrangements are also contemplated. The absorber springs 62, 64 act to absorb load from the medial compartment of the knee while the articulation of the ball/sockets and the telescoping of piston assemblies of the absorber allow the device to accommodate full knee range of motion.

For best performance of the joint unloading system 50, the femoral base 52 and the associated ball and socket articulating surfaces at the femoral end 66 of the joint unloading device 60 should be precisely positioned. In order to more easily locate the accurate position for this proximal base 52 and articulation a position verification tool and related method have been developed.

Conventional or surgical or minimally invasive approaches are taken to gain access to a body joint or other anatomy requiring attention. Arthroscopic approaches are contemplated when reasonable to both implant the energy manipulation assembly as well as to accomplish adjusting an implanted assembly.

In one approach for treating a knee, an implantable extra-articular energy absorber system is designed to reduce medial compartment loads of the knee. The absorber system is comprised of two contoured base components, a kinematic load absorber and a set of bone screws. The implanted system is both extra articular and extra capsular and resides in the subcutaneous tissue on the medial aspect of the knee. The device is inserted through two small incisions superior to the medial femoral condyle and inferior to the tibial plateau. The contoured base components are fixed to the medial cortices of the femur and tibia using bone screws.

An energy absorber 60 having a spring value of about twenty pounds can provide therapeutic benefit for patients of 300 pounds or less. Higher spring forces would provide greater reduction in joint load and may correlate to greater symptom (i.e., pain) relief.

It has been found that a medial compartment of a knee of an average person with osteoarthritis can benefit from an absorber set for compression between 1 mm and 10 mm, and preferably 3-6 mm with a spring or absorber element that accommodates a range from 20-60 pounds. In one preferred embodiment, the absorber is set for about 4 mm of such compression and a pre-determined load of about 40 pounds. An absorber of 40 pounds load absorption can unload the medial compartment of a patient's knee from 25-40 pounds.

The femoral and tibial base components can be contoured to ensure optimal fit to the bony surfaces and can be plasma sprayed coated with porous titanium and/or coated with hydroxyapatite on bone contacting surfaces to promote bony ingrowth and enhance osteointegration.

Figure 3:
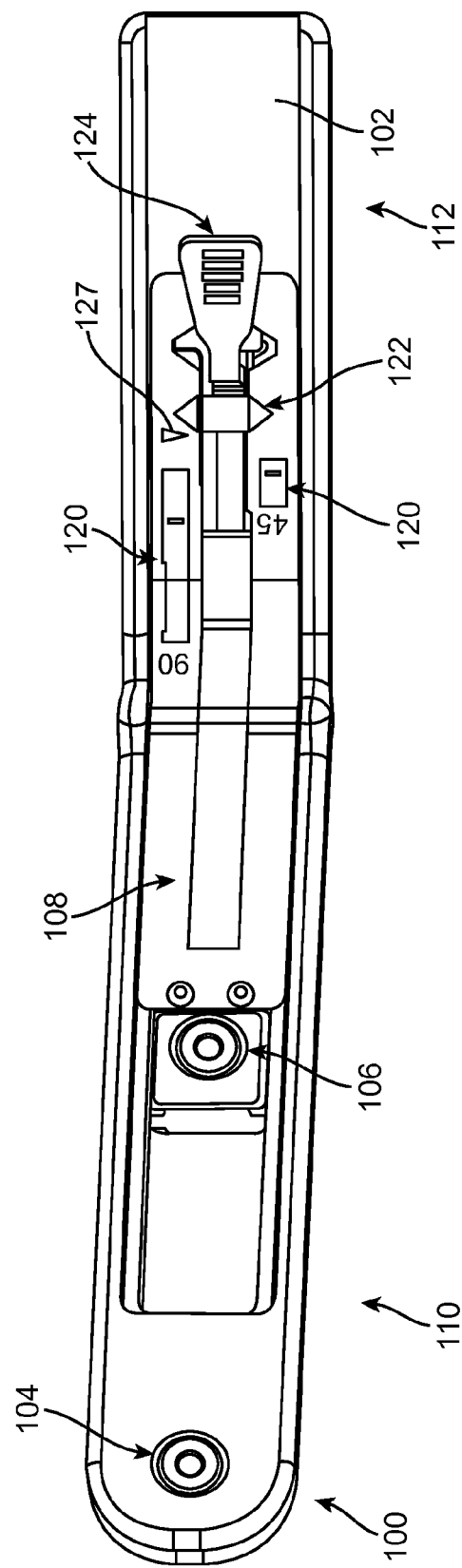
FIG. 3 is a side view, of a position verification tool for location of a correct position for the joint unloading system of FIG. 1.
Figure 4:
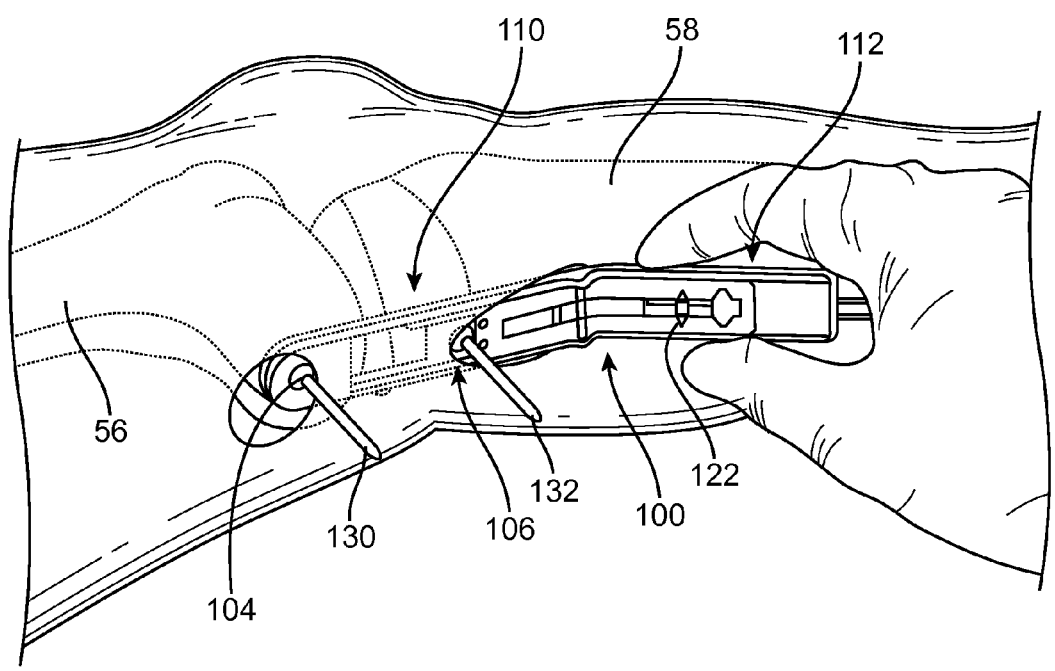
FIG. 4 is a perspective view, of the verification tool of FIG. 3 in use on a patient.
Figure 5:
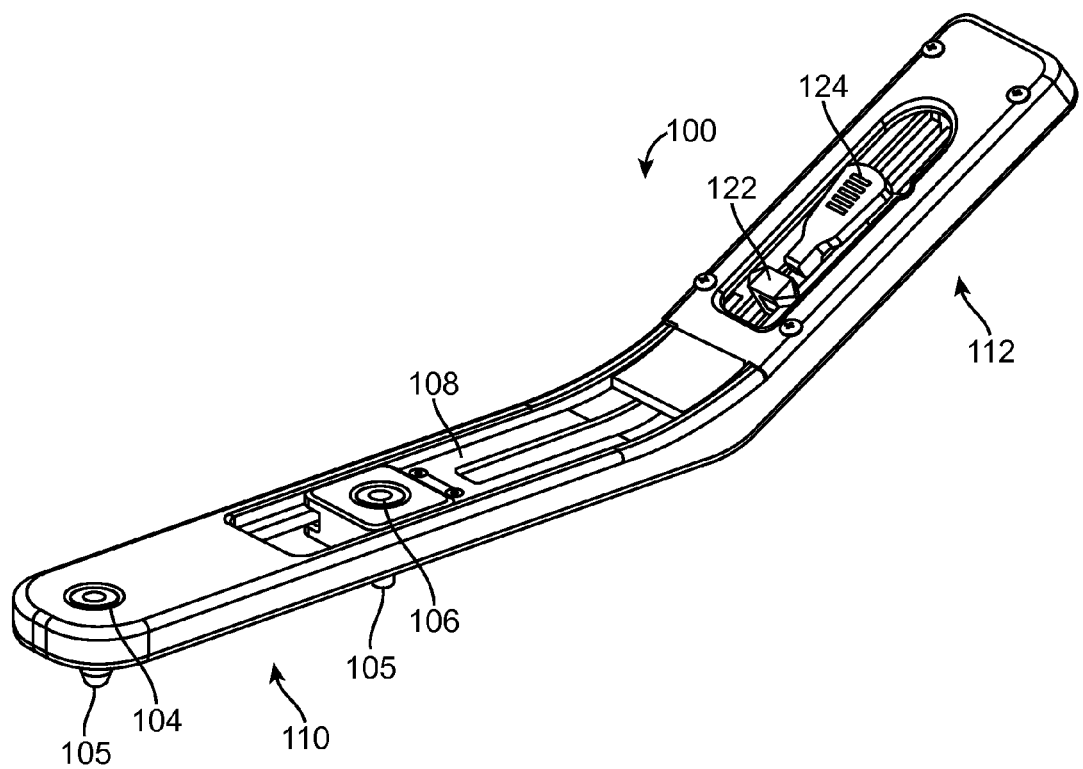
FIG. 5 is a perspective view, of the verification tool of FIG. 3.

The position verification tool 100 shown in FIGS. 3-5 is used during surgery to verify a position of the femoral base 52 and the femoral articulation surface of the absorber 60 to achieve the most functional position of the system 50. The preferred implantation position of the system 50 is achieved when the springs 62, 64 are in a compressed orientation during the swing phase of the gait including full extension and low flexion angles of the knee joint. The springs are in a less compressed or in an uncompressed position at 45 degrees of flexion of the knee, and by 90 degrees flexion of the knee the springs are preferably uncompressed or nearly uncompressed. This configuration corresponds to the composition of the gait cycle where the largest forces are exerted on the knee joint near full extension and these forces are greatly decreased when the knee is flexed during the swing phase of the gait.

The position verification tool 100 as described herein verifies that the desired motion will occur for the particular design of a particular joint unloading system which is to be implanted. Although the position verification tool 100 has been described for use with the joint unloading system 50, it should be understood that the verification tool can also be used to verify fixation positions of other implantable systems are designed to have a particular desired kinematic pattern as a joint moves through a particular range of motion.

The position verification tool 100 is used in a method of implanting the joint unloading system 50 by inserting first and second reference markers into first and second bones on opposite sides of the joint and connecting the first and second reference markers to the verification tool. The verification tool 100 then is used to determine whether the first and second reference markers move in a desired kinematic pattern with respect to one another. Examples of kinematic patterns include 1) reference markers moving away from each other as the joint moves from extension to flexion; 2) reference markers staying within a certain defined distance of each other as the joint moves from extension to flexion; 3) reference markers moving toward each other as the joint moves from extension to flexion; and 4) reference markers moving away from each other and then toward each other as the joint moves.

In addition to verification of the position for placing one or more of the bases 52, 54, the position verification tool 100 can also be used to select an joint unloading member 60 when different sizes or configurations of joint unloading members are available, such as those as described in U. S. Patent Publication No. 2009/0014016.

The position verification tool 100 includes a body 102 having a first end 110 for attachment to reference markers in the patient and a second gauge end 112 which extends at an angle from the first end for monitoring relative motion of the reference markers and the bones. The first end 102 of the tool 100 has a first connection point 104 with a fixed longitudinal location on the body. The first connection point 104 may include a guide hole and a guide ball which allows a marker to pivot within the tool body 102 but does not allow the first connection point to translate. The first connection point may also include an offset 105, shown in FIG. 5, which causes the tool to sit off the bone by a distance of the offset allowing the tool to rotate more easily without interference from the bone. The tool 100 has a second connection point 106 with a longitudinally movable location. The second connection point 106 may also include a guide hole through a guide ball which allows a marker to pivot within the tool body 102. The guide ball at the second connection point 106 may also include an offset 105. The guide balls allow the tool 100 to rotate about the first and second reference markers or K-wires throughout the range of motion of the joint even when the reference markers are not exactly parallel.

The second connection point 106 is secured to a flexible ribbon 108 which is longitudinally movable on the tool 100. The flexible ribbon 108 acts as a gauge to monitor the relative motion of the reference markers while moving the joint through a predetermined range of motion. Thus, the second connection point 106 moves longitudinally on the verification tool 100 as the joint is moved through a range of motion. The verification tool 100 is used to determine whether the first and second reference markers move in a desired kinematic pattern with respect to one another throughout the predetermined range of motion. As discussed above, the desired kinematic pattern may be a pattern where the reference markers move apart as the joint moves from extension to flexion. If the desired kinematic pattern is not achieved, one of the reference markers is relocated. The verification tool may then be used to check the new position.

Other configurations of the verification tool 100 are also contemplated in which the motion between the first and second connection points 104, 106 is accommodated and verified in other manners. For example, a telescoping verification tool 100 may be used including bars or identifying bands on a portion of the telescoping parts.

Figure 6A:
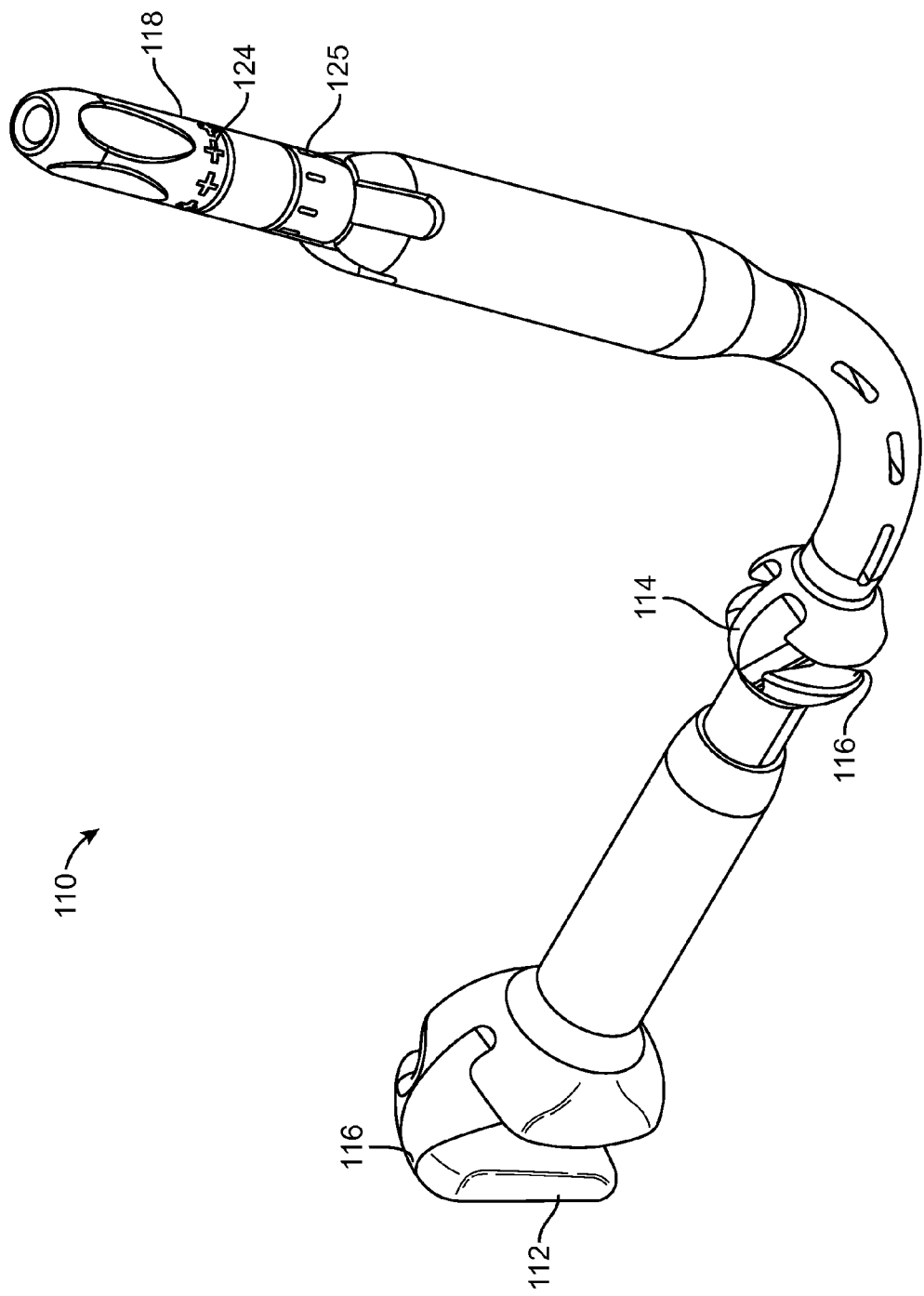
FIG. 6A is a perspective view, of alternative approach to a verification tool.
Figure 6C:
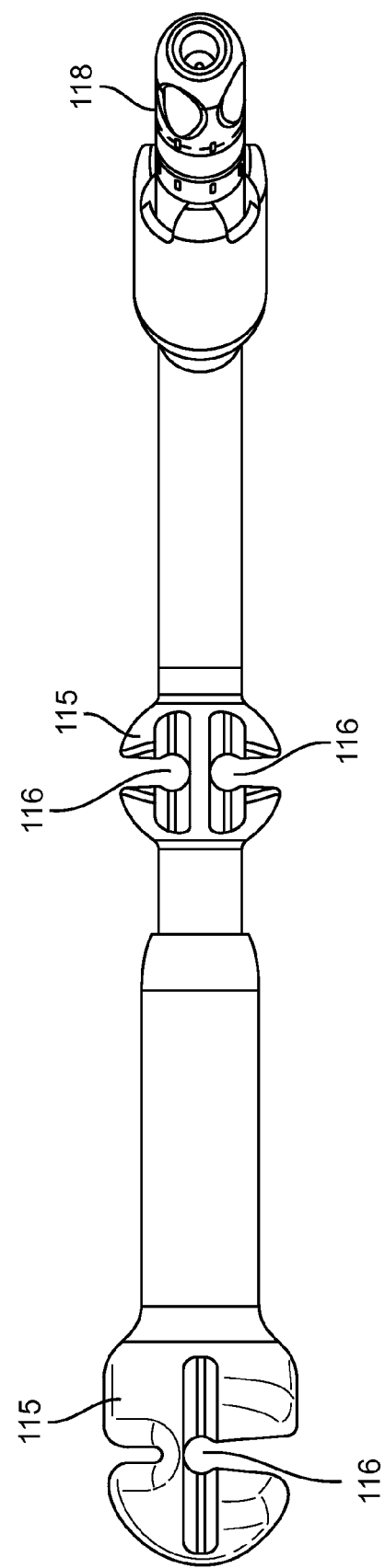
FIG. 6C is a top view, depicting the verification tool of FIG. 6A.

In an alternative approach, as shown in FIGS. 6A-C, a kinematic verification tool 110 can be embodied in an elongate device. The tool 110 includes a femoral side assembly 112 and a tibial side assembly 114. As best seen in FIG. 6B, the femoral side assembly 112 includes an internal bore sized and shaped to receive a length of the tibial side assembly 114. The femoral side assembly 112 is generally straight and the tibial side assembly includes a curved or flexible mid-section. It is to be appreciated that the femoral and tibial side assemblies 112, 114 are rotatable and longitudinally translatable with respect to each other. They each further include enlarged sections 115 including slots 116 for receiving K-wires or other referencing structure projecting from the femur and tibia, respectively. The enlarged section 115 of the tibia side assembly 114 can include two such slots 116 for receiving referencing structure. Such slots are configured to provide convenient snap-on connections with referencing structure, in that referencing structure can be snapped into the enlarged section 115 by moving the tool 110 laterally with respect thereto.

The kinematic verification tool 110 further includes a handle insert 118 configured within a bore extending through the tibial side assembly 114. Again, as best seen in FIG. 6B, a screw 120 is contained within the handle insert 118. The screw 120 is connected to a wire 122, such as a Nitinol wire, that extends through the verification tool 110 to the femoral side assembly 112. This connection between the handle insert 118, screw 120 and wire 122 allows the tool 110 to track the relative motion of the femoral and tibial assemblies. The handle insert additionally includes indicators 124, 125 which facilitate observing the kinematic pattern of the tibial and femoral reference markers on which the tool 110 has been secured. Where the tibial and femoral reference markers moving away from each other this motion will be reflected as positive movement in the indicators 124. Where the tibial and femoral reference markers move toward one another during motion of the joint the indicators 125 indicate a negative motion.

In one approach to a surgical method, an initial step in treatment involves identifying a patient's Blumensaat's line, which is a radiographic and structural feature of a femur. Using Blumensaat's line as an anatomical radiographic landmark, an acceptable region and target area can be identified for placement of a center of rotation of a femoral socket just anterior and/or proximal of the center of rotation of the femur. As shown in FIG. 4, a reference marker 104 or K-wire is positioned in the femur under fluoroscopy or another imaging technique. The placement of the femoral reference marker 104 can be done manually without the assistance of a placement tool. Alternatively, a bullseye tool guide 200 or other placement tool may be used to insert the reference marker 104 at a desired target area.

Figure 7A:
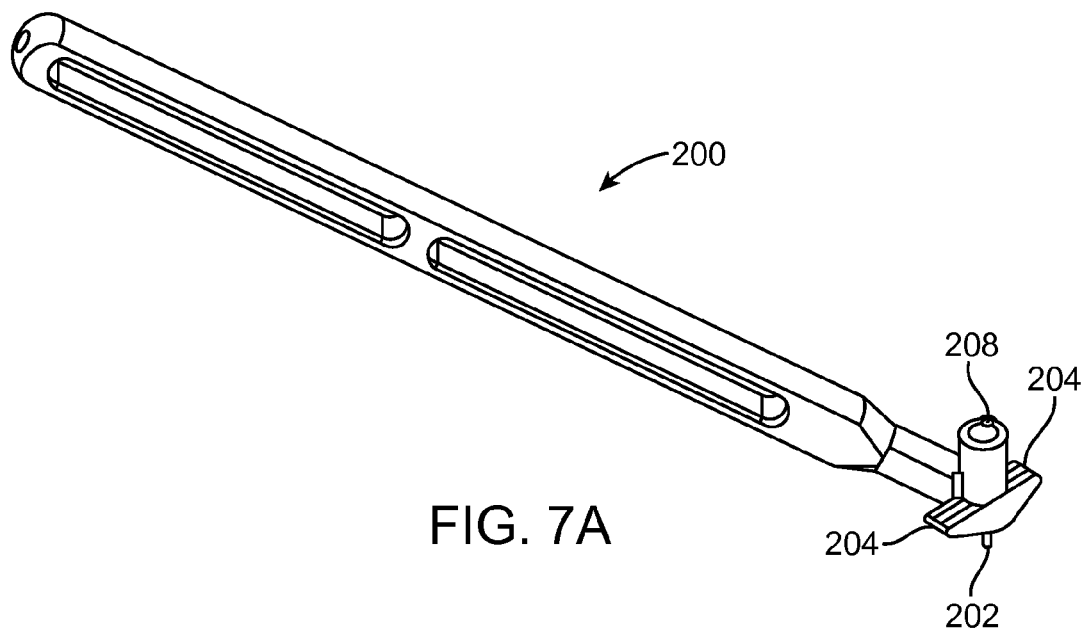
FIG. 7A is a perspective view of a bullseye tool for inserting a reference marker into a bone at a desired location.
Figure 7B:
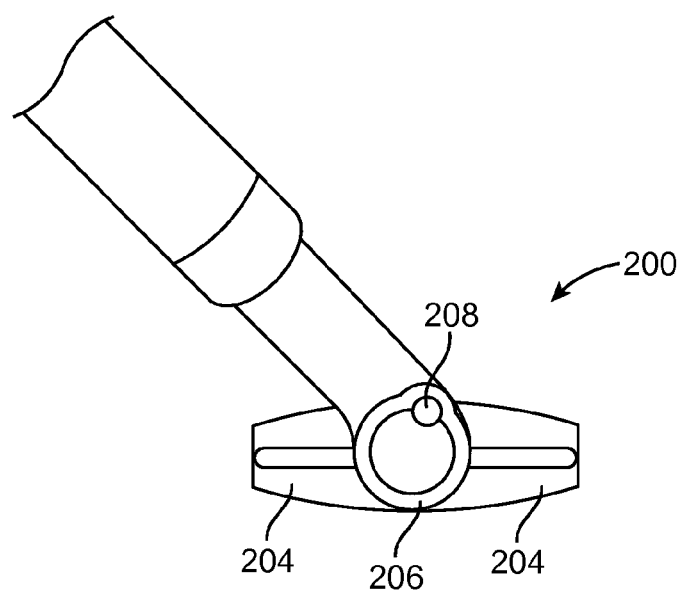
FIG. 7B is a top view of a portion of the bullseye tool of FIG. 7A.

The bullseye tool 200 shown in FIGS. 7A and 7B is employed as a guide through which a K-wire 130 is inserted into the femur either through the patient's skin or after making a small incision. It is to be noted that anatomical and/or radiographic landmarks (e.g., center of Blumensaat's line, inferior and posterior regions of the femoral condyles) can aid in manually positioning a K-wire in the target region or location, with or without the bullseye instrument. The bullseye tool is used for locating a center of rotation of the femoral socket by locating an anatomical reference location, such as the center of Blumensaat's line, and locating the center of rotation of the implant a predetermined distance and direction from the anatomical reference location.

When using the bullseye tool 200, the bullseye tool is placed with a center pin 202 of the bullseye tool on the midpoint of Blumensaat's line. The tool is rotated until two wings 204 of the tool (with radiopaque markers) are parallel to Blumensaat's line. Vertically spaced apart radiopaque rings 206 are arranged in the center portion of the bullseye tool 200 and when these rings are aligned (concentric) in a the bullseye tool is perpendicular to the fluoroscopic view and properly aligned to insert a reference marker 130 perpendicular to the lateral view. In this position, the K-wire or reference marker 130 is placed through a hole 208 in the tool 200 to locate the center of rotation of the femoral socket of the joint unloading device 60. The hole 208, a shown, has a trajectory which is parallel to the direction of imaging when the concentric rings are aligned. However, other trajectories of the reference marker 130 may be achieved by varying the trajectory of the hole in the bullseye tool 200.

The location of the hole 208 in the bullseye tool 200 is designed to be just anterior and proximal of the midpoint of Blumensaat's line when the tool is positioned as described above. Since it has been shown that the midpoint of Blumensaat's line is a good radiographic approximation of a center of rotation of the femur, the location of the reference marker 130 anterior and proximal of this midpoint of Blumensaat's line has been shown to be a starting point for finding a location of the center of rotation of the femoral articulation and achieving a desired kinematic pattern where the reference markers move apart as the joint moves from extension to flexion.

Figure 7C:
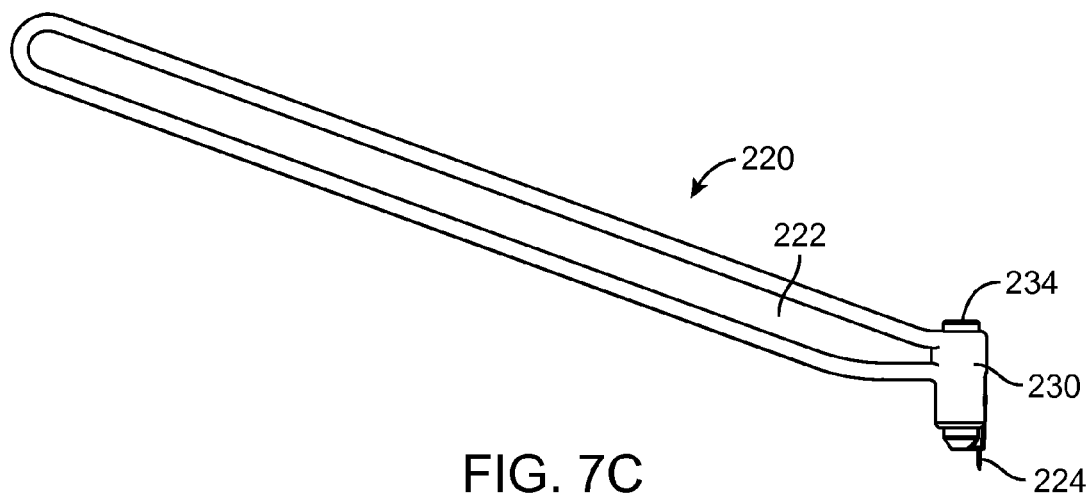
FIG. 7C is a side view of an alternative embodiment of a bullseye tool.
Figure 7D:
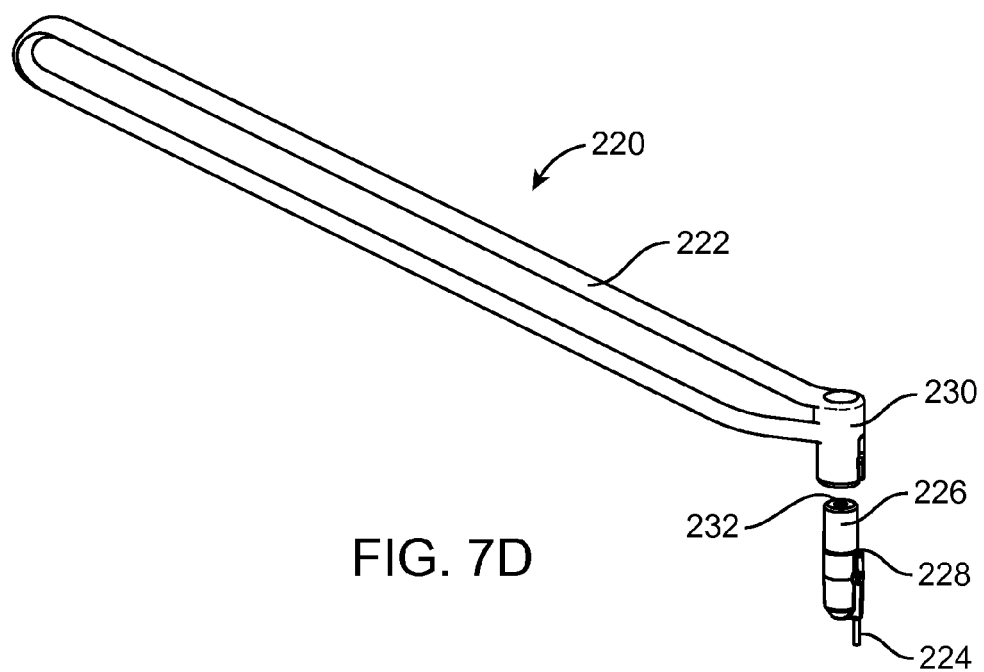
FIG. 7D is an exploded perspective view of the bullseye tool of FIG. 7C.

FIGS. 7C and 7D show an alternative embodiment of a bullseye tool 220 having a handle 222 and a separable tip 226. The bullseye tool 220 has a lumen 232 for receiving a K-wire or other reference marker and a ring shaped radiopaque marker 228 concentrically surrounding the central lumen 232. A pin 224 is provided on the tip 226 for holding the tip of the bullseye tool in place while the reference marker is inserted into the bone. The tip 226 can be snapped out of the handle 222 for disposal in a sharps container by pressing on a button 234 formed by the upper surface of the tip 226.

Figure 8A:
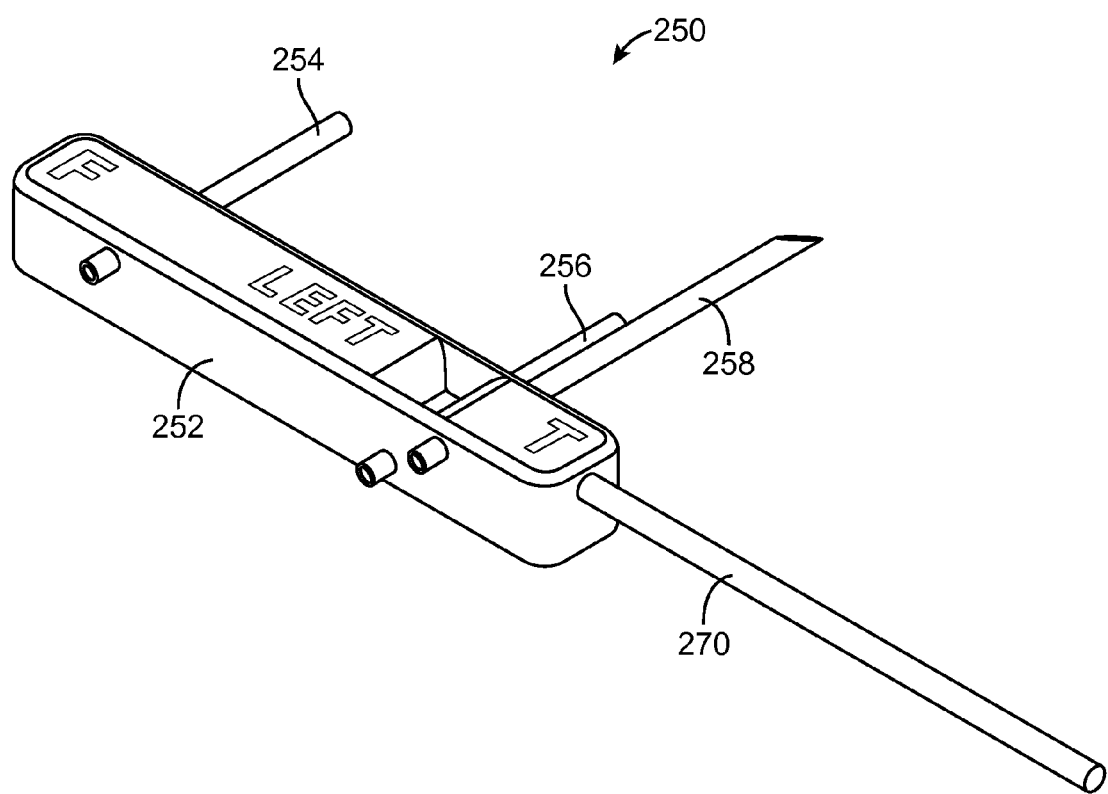
Figure 8B:
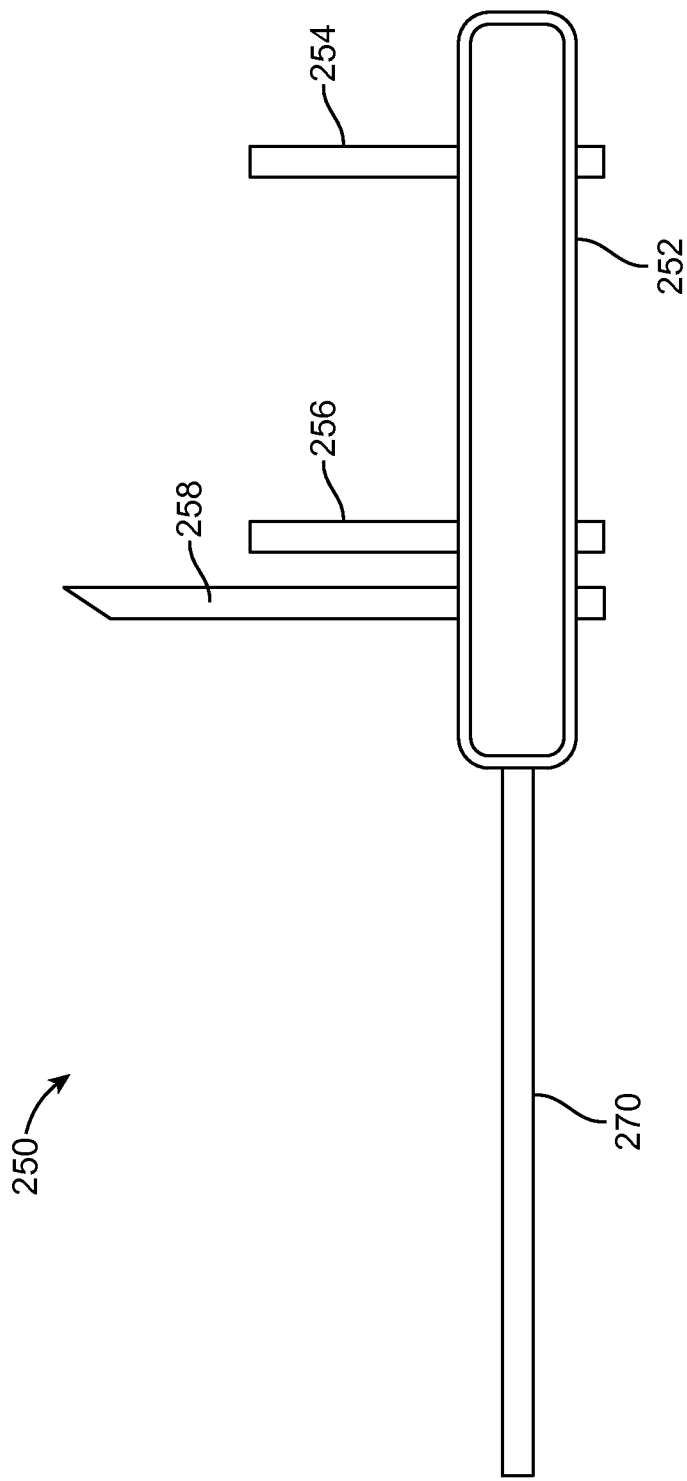
Figure 8D:
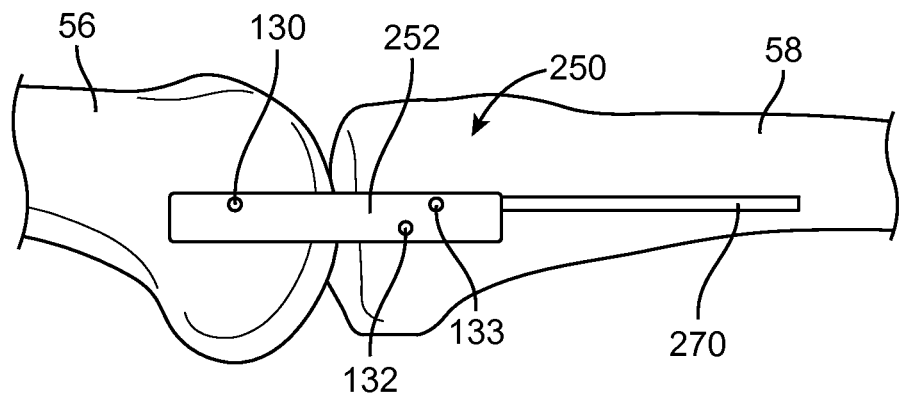
FIG. 8D is a side view, depicting the alignment guide assembly of FIGS. 8A-C in use.
Figure 8E:
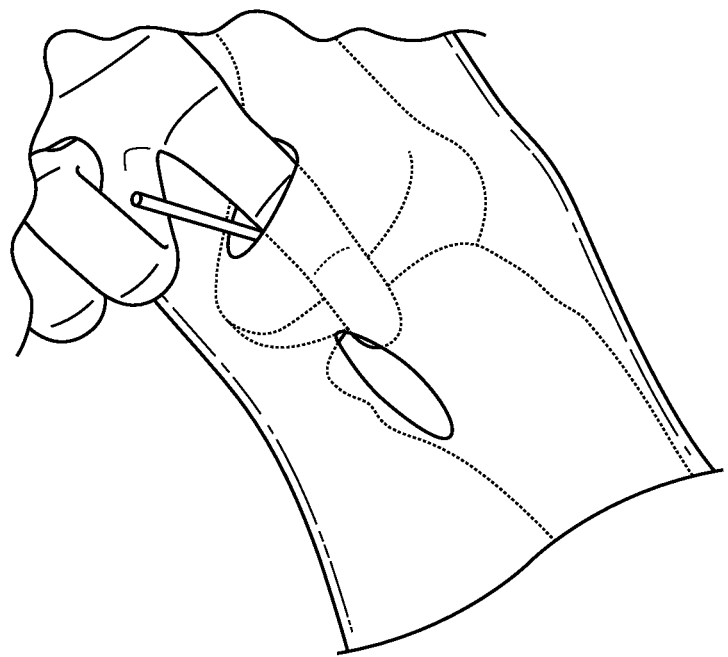
FIG. 8E is a perspective view, depicting forming a tunnel between incision sites.

Next, with reference to FIGS. 8A-E, an alignment guide 250 can be employed to facilitate aligning a femoral trial and an absorber, as well as to properly position the absorber while securing a tibial base. The alignment guide 250 has a generally rectangular shaped body 252. Extending substantially perpendicular to a long dimension of the body 252 are a plurality of tubes 254, 256, 258 for inserting reference markers or K-wires into the bones of a joint to position these reference markers at desired relative positions. A first tube 254 is sized and shaped to receive the femoral reference marker 130. The second and third tubes 256, 258 are configured to receive reference markers (i.e. item 132) extending from the tibia. The reference markers are generally in the form of K-wires which may be provided in differing lengths. An indicator rod 270 is further provided on the alignment guide 250 and is configured to extend longitudinally from an end of the body 252 nearest the second and third tubes 256, 258. As shown in FIG. 8A either the second or third tube 256, 258 may include an angled tip which functions to penetrate the bone slightly to maintain the alignment guide 250 in position while reference markers are driven into the bone.

In use, the patient's leg is straightened and a confirmation is made to ensure that the knee is extended. The placement guide 250 is then placed such that the first tube 254 is positioned in a femoral incision and about the femoral reference marker 130 which has been positioned as described above. The body 252 of the placement guide is designed to reside outside of the tissue of the patient while the tubes 254, 256, 258 extend into the surgical site. The indicator rod 270 is aligned so that it is parallel to the tibia axis (See FIG. 8D) under fluoroscopy. An incision is then made between the second and third tubes 256, 258 to provide access to the tibia. It is contemplated that the incision length is 5-8 cm. Next, a tissue tunnel is created using blunt dissection between the two incisions sites (See FIG. 8E). The tunnel width is formed so as to accommodate an absorber.

With the knee in an extended position, confirmation is again made that the indicator rod 270 remains parallel to the tibial axis. A first tibial reference marker 132 can be inserted into the second tube 256 of the alignment guide 250. The second tibial reference marker 133 is then placed through the third tube 258. It is to be recognized that the location of the tibial ball of an absorber will be at the third tibial reference 133. The first and second tibial reference markers 132, 133 will assist in the femoral base selection and alignment. In addition, the tibial reference markers 132, 133 can be employed to support the absorber prior to tibial base fixation.

As shown in FIG. 4, the verification tool 100 is inserted through a tissue tunnel between first and second incisions in the leg on opposite sides of the knee joint. The tool is placed onto the first reference marker 130 positioned in the femur and a second substantially parallel reference marker 132 is placed through the connection point 106 of the tool into the tibia. The distance between the first connection point 104 and the second connection point 106 on the verification tool 100 is selected to provide the desired spacing for mounting bases to the bones to accommodate the joint unloading member 60. Although the verification tool 100 has been described as operating partly beneath the patient's skin within a tissue tunnel, it should be understood that in some cases the verification tool may be entirely underneath or entirely outside of the patient's skin.

The verification tool 100 includes one or more bars, bands, grids or other markings, such as the 45° and 90° bars 120 shown in FIG. 3 as well as a pointer 122. The 45° bar shows the range of acceptable locations of the pointer 122 when the joint is at 45° of flexion, while the 90° bar shows the range of acceptable locations of the pointer when the joint is at 90° of flexion. The bars are merely shown by way of example as one or more other bars may also be used. The bars are merely a simplified way of determining if there is not enough or too much space between the reference markers as the joint is articulated. If there is not enough or too much spacing between the reference markers, this in an indication that one or both of the reference markers should be moved to achieve the best function of the joint unloading device 50.

In one embodiment of the invention, the location of the femoral reference marker is verified by placing the verification tool on the femoral reference marker 130 as shown in FIG. 4 and inserting the tibial reference marker 132 through the connection point 106. When placing the tibial reference marker 132, the pointer 122 should be pointing at the zero mark 126. To simulate stance or loaded extension, the knee should be located in extension and any medial laxity in the joint should be removed by pulling the tibia medially to close the medial joint space during placement of the tibial reference marker 132. In the event that the knee joint was not in full extension or the medial joint space was partially open during placement of the tibial reference marker, the verification tool 100 can be readjusted to the zero mark 126 after correcting the knee position. To verify the femoral reference marker location, the knee is flexed through a range of motion while the location of the pointer 122 with reference to the bars 120 on the verification tool 100 is observed. For example, when the knee is moved from extension through 45° of flexion with the medial joint space closed the pointer position should be within the 45° bar. In addition, when the knee is moved from extension through 90° of flexion with varus, valgus, internal and external rotations, the pointer position should be within the 90° bar. If this verification is successful, the verification tool 100 can be removed and the femoral reference marker 104 is confirmed to be at the desired location for the center of rotation of the femoral articulation 66. If the pointer moved outside of the bars during the prescribed motion, the femoral reference marker location should be adjusted as described below. This verification is performed under direct visualization.

The following guidelines can be used to move the femoral reference marker 130 if the criterion of the verification tool 100 are not met. If the pointer never enters either the 45° or 90° bar during the verification steps or if the pointer travels outside the bounds of either of the 45° or 90° bars during the specified flexion angles, a new reference marker should be inserted at a location displaced a short distance from the original reference marker 130. In the case of the pointer never entering either the 45° or 90° bar during the verification steps, the new reference marker should be inserted in a region which is distal and/or anterior to the original marker a distance of about 1-2 mm. If the pointer travels outside the bounds of either of the 45° or 90° bars (moves completely past the bars) during the verification steps, a new reference marker should be inserted in a region which is posterior to the original marker. The original femoral reference marker 130 is then removed and the verification test is repeated with the new relocated reference marker. The tibial reference marker 106 does not need to be moved as the verification tool 100 can be readjusted to the zero position after the new femoral reference marker 104 is inserted.

In the event that multiple joint unloading devices 50 are available, i.e. different sizes, the verification tool may include additional markings or may come in different sizes.

Although the verification tool 100 has been illustrated as using the visual analog reference of the pointer 122 and the bars 120, it should be understood that other methods may alternatively or additionally be used for verification feedback. For example, the verification tool 100 can include visual, auditory, tactile, and/or digital feedback. Moreover, the verification tool 110 depicted in FIGS. 6A-C can alternatively be employed to assess the kinematic pattern of the reference markers and provide verification feedback. The verification tool 110 of FIGS. 6A-C has the advantages of having a simpler connection via a snap on connection to the reference markers and easier interpretation with a longer and flexible location for the indicia.

Once an acceptable position of the reference marker 130 is verified the joint unloading device 50 is implanted across the joint by locating the bases 52, 54 on the bones employing the instruments and methods which will be described below. Particularly, the femoral base 52 is located at a preferred location with respect to the location of the reference marker 130 to locate the center of rotation of the femoral articulation 66 at the location of the reference marker.

Figure 9A:
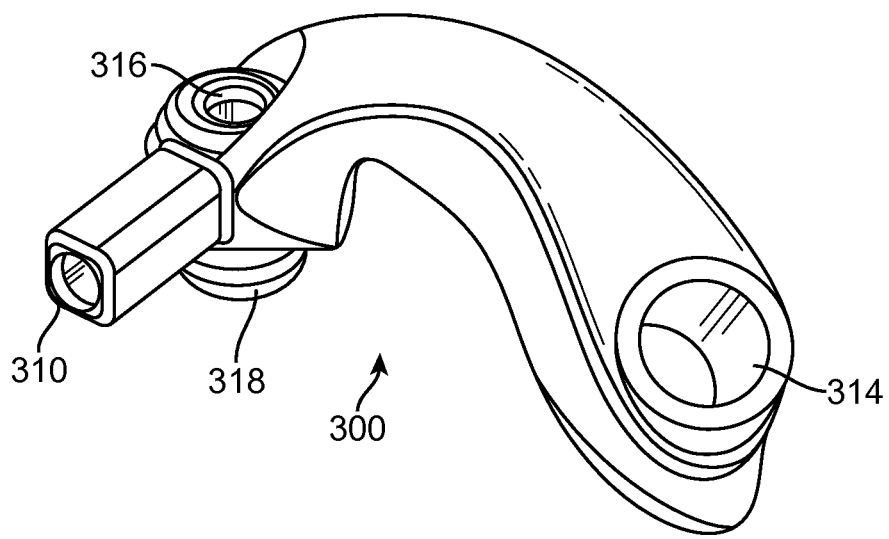
FIG. 9A is a top perspective view of a placement guide used to facilitate correct positioning of the base.
Figure 9B:
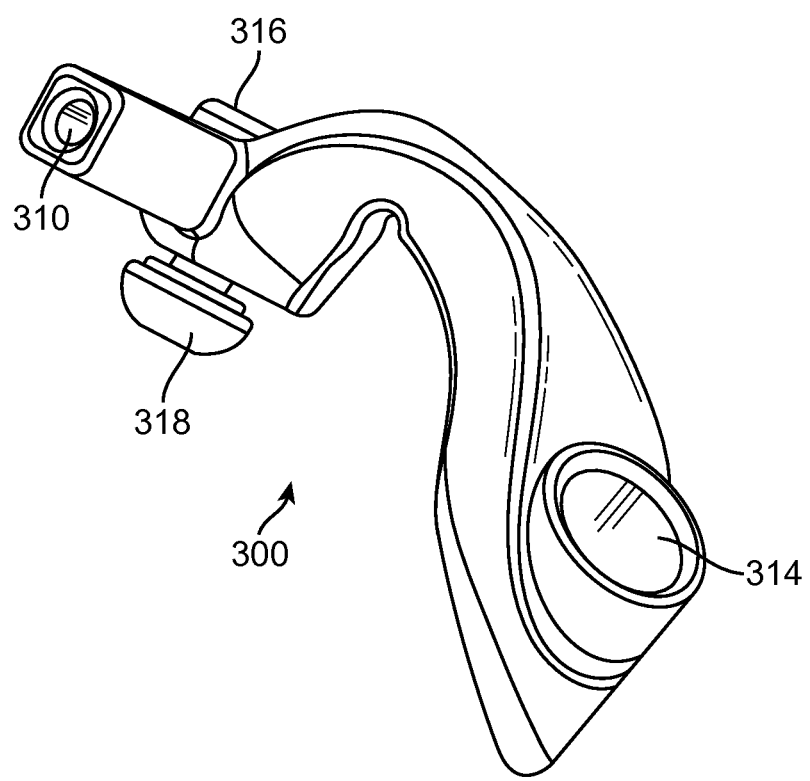
FIG. 9B is a side perspective view of the placement guide of FIG. 9A.
Figure 10:
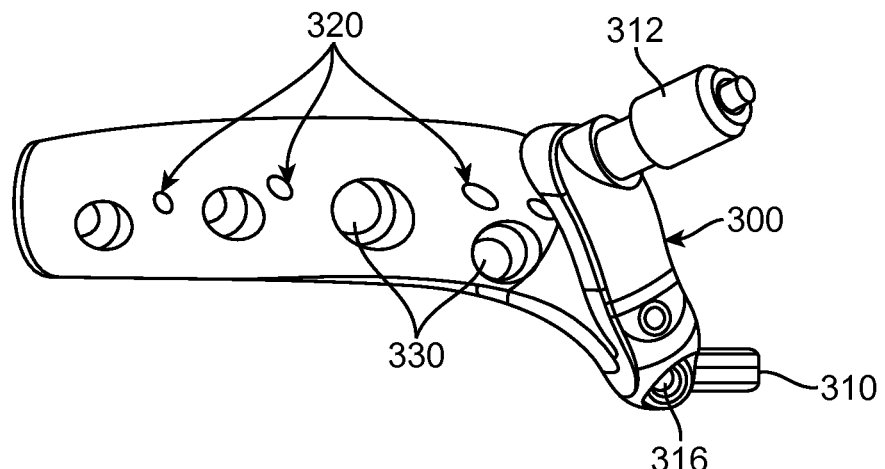
FIG. 10 is a top view of the placement guide of FIG. 9A temporarily attached to a base.

To assist in location of the femoral base 152, a femoral placement guide 300 shown in FIGS. 9A, 9B and 10 is temporarily attached to the femoral base 152. To ensure that the femoral base 152 stays at a correct location during attachment to the bone, the femoral placement guide 300 is configured to temporarily attach to the base and later be removed after attachment is complete. The placement guide 300 is attached to a selected femoral base 152 by a guide knob 312 (FIG. 10) which fits into the large distal hole 314 of the guide 300 and threads into a bone screw hole 330 of the base. The placement guide 300 includes a proximal guide hole 310 into which a K-wire or other elongated member can be inserted for positioning. The placement guide also includes a hole 316 with an offset 318 for receiving the reference 130 which was placed in the previous steps. The configuration of the hole 316 and offset 318 is designed to locate the femoral base 152 at a position where when the absorber 60 is attached to the femoral base, the absorber femoral articulation 66 will be located to achieve the desired kinematics. Specifically, the location of the hole 316 with respect to the base 152 corresponds to the location of the femoral articulation 66 with respect to the base when the absorber 60 is attached to the base. Additionally, the offset 318 corresponds to a desired offset of the absorber femoral articulation 66 from the bone. A height of the offset 318 is preferably at least 2 mm to provide sufficient clearance between the ball and socket articulation of the absorber and the bone when the absorber is connected to the base.

Figure 11:
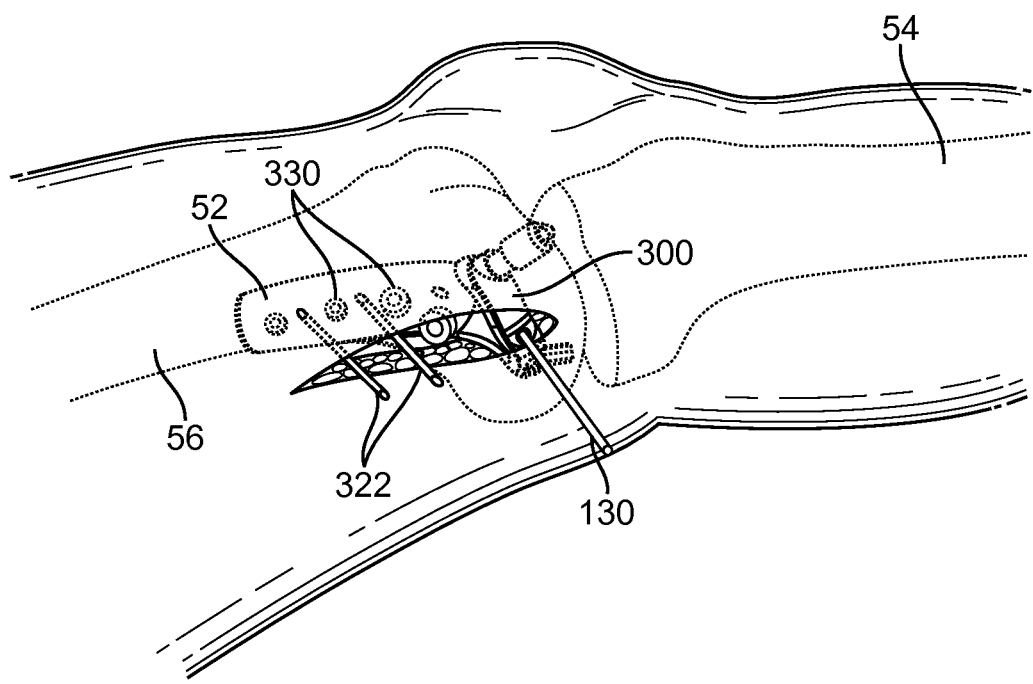
FIG. 11 is a perspective view of the placement guide and base as they are positioned for attachment of the base to a bone of a patient.
Figure 12:
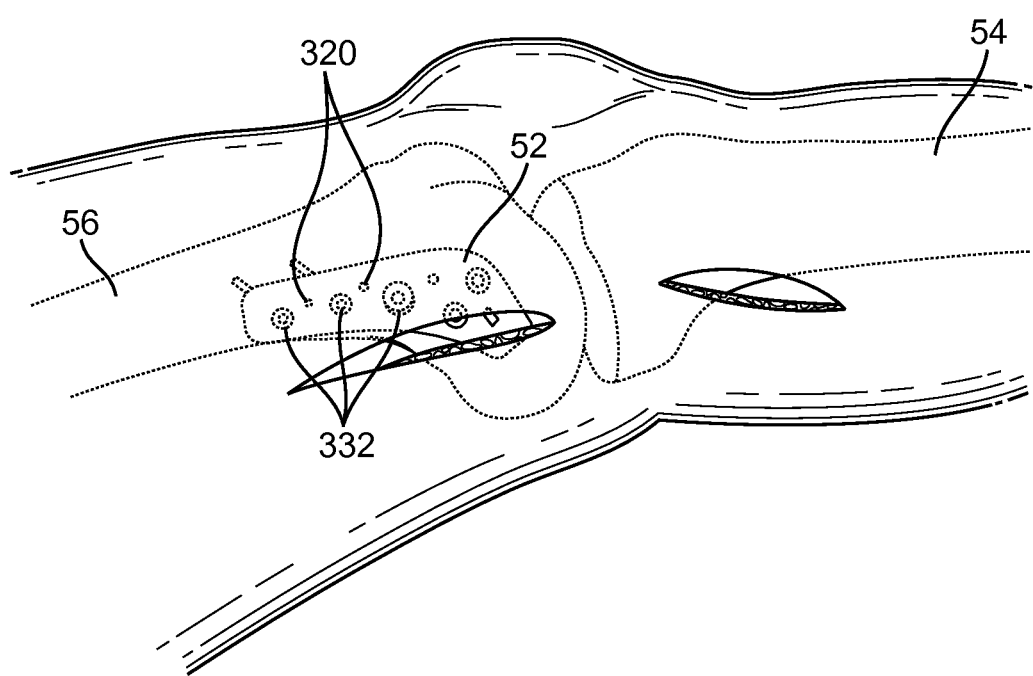
FIG. 12 is a perspective view of the base attached to the bone of a patient with the placement guide removed.

As shown in FIG. 11, the femoral base 52 with the attached placement guide 300 are placed onto the femur by sliding the placement guide hole 316 over the previously placed reference marker 130. A proper position of the femoral base 52 can be determined by placing a guide wire into the guide wire hole 310 of the placement guide 300. The guide wire should extend generally perpendicular to the tibial plateau and generally parallel to the medial femoral condyle. The femoral base 52 is held in place by inserting one or more, and preferably two or more, K-wires 322 through the available K-wire holes 320 in the femoral base. These K-wires 322 will hold the femoral base 52 in place during placement of the bone screws 332 through the bone screw holes 330. The bone screws may include combinations of unicortical cancellous compression screws, locking screws, and bicortical compression screws. The screws may be placed before or after removal of the placement guide 300 from the base 52. Preferably, the placement guide is removable from the base 52 by removing the guide knob 312 after the base is secured to the bone by bone screws. FIG. 12 illustrates the placement of the femoral base 52 after the placement guide 300 has been removed. Once the femoral base 52 is secured to the bone, the base is ready for attachment of the absorber 60 and securing of the tibial base 54.

The femoral base 52 can be provided in different shapes and/or sizes as well as versions for left and right knees. The femoral placement guide 300 can be provided in versions which coordinate with the different bases. In addition, in the event that different absorber configurations are available, the placement guide 300 can be provided in different versions to accommodate the absorbers.

In addition to or as an alternative to the femoral placement guide 300, trial bases can be used to located a desired orientation and position of the femoral base 52. For example, a trial base in the form of a one piece member having a shape of the combination of the base and placement guide shown in FIG. 10 can be used to determine and mark a position for the placement of the base. In the case of a trial base, the trial can include the offset to determine correct spacing of the articulation from the bone and can include the guide wire hole to aid in determining angular position with respect to the joint surfaces.

In one embodiment, once the femoral base 52 has been secured to the bone the absorber 60 with the attached tibial base 54 is inserted through a tissue tunnel between the skin and bone of the patient and the socket 66 of the absorber is connected to the femoral base 52. Methods and instruments for connecting the absorber sockets 66, 68 to the bases 52, 54 are shown and described in further detail in US Patent Publication No. 2009/0014016. Such connection of the sockets to the bases may be by taper locks, locking pins, locking screws and the like. Once the absorber 60 has been connected to the femoral base 52, the system is ready for attachment of the tibial base 54 to the tibia of the patient.

Figure 13A:
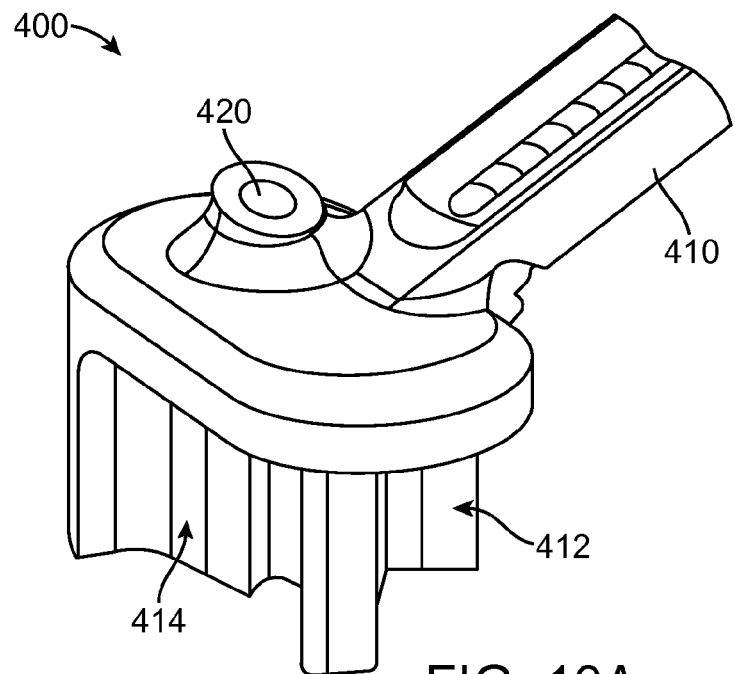
FIG. 13A is a side perspective view of an absorber positioning collar.
Figure 13B:
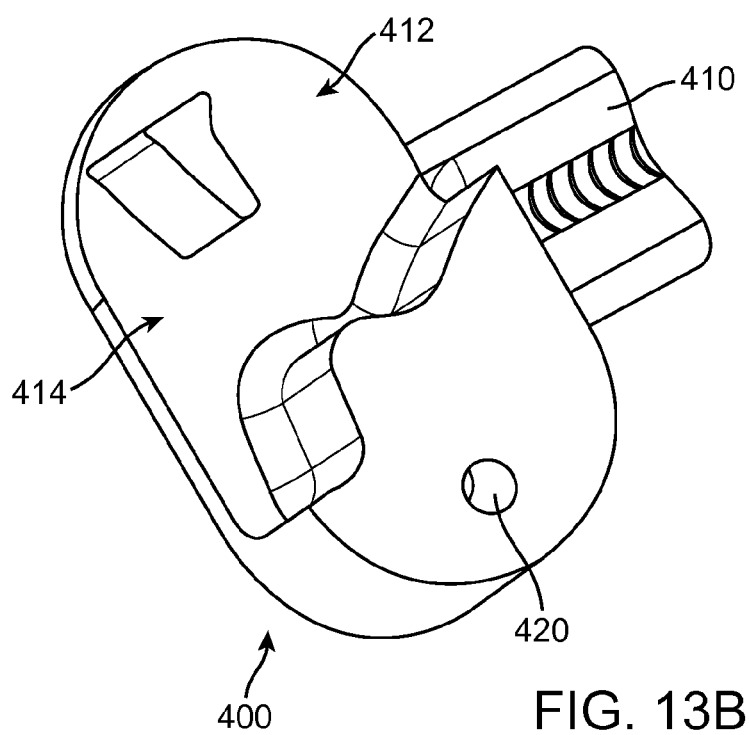
FIG. 13B is a bottom perspective view of the absorber positioning collar of FIG. 11A.

To assist in proper alignment and positioning of the absorber 60 and positioning of the tibial base 54, an absorber positioning collar 400 is shown in FIGS. 13A and 13B. Setting the trajectory of the femoral bearing 66 is important to achieve desired motion of the absorber relative to the motions of the knee and the implantable system. If the bearing resides in an inappropriate plane then one of the ball/sockets can have insufficient motion in at least one direction. The absorber positioning collar 400 includes a handle 410, a femoral base receiving recess 412, and a femoral socket receiving recess 414. The positioning collar 400 also includes an optional K-wire hole 420 for temporarily securing the positioning collar in place. The absorber positioning collar 400 is designed to be temporarily located between the femoral base 54 and the femoral socket 66 to aid in positioning. The collar 400 sets the absorber position relative to the implanted base 52. Since anatomies vary, the collar 400 may be configured to fix the absorber position or to allow some limited range of angles of the absorber with respect to the base. For example, where a total range of motion of the articulation is greater than 100 degrees, the motion may be limited by the collar 400 for purposes of initial positioning to less than 45 degrees, and preferably about 20 degrees or less.

In addition to setting the absorber angular position, the collar 400 can include one or more features for setting a desired range of offset distances between the absorber and the underlying bone.

Figure 14:
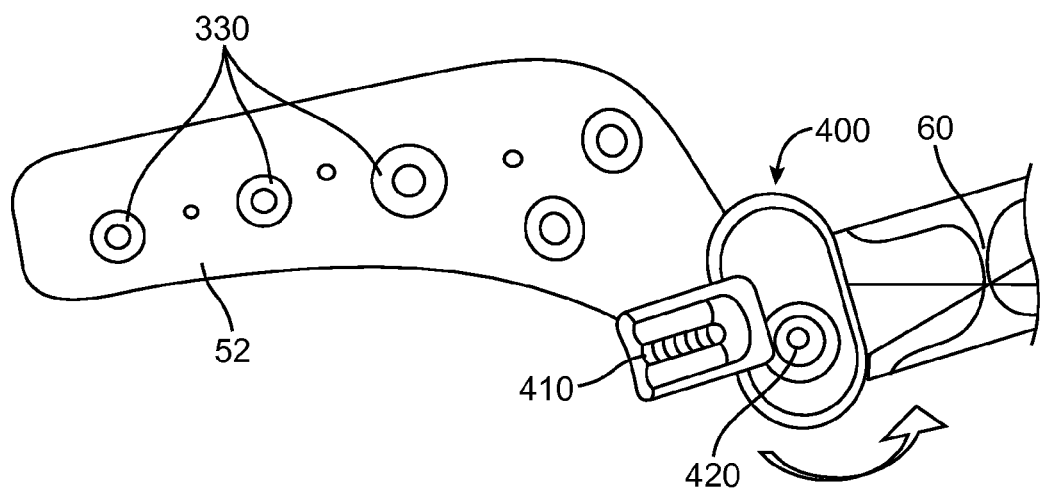
FIG. 14 is a top view of the positioning collar of FIG. 13A positioned between a base and absorber.

As shown in FIG. 14, the absorber positioning collar 400 is placed onto the femoral socket 66 of the absorber 60 with the recesses 412, 414 receiving the distal end of the femoral base and the femoral socket, respectively. The positioning collar 400 temporarily limits motion of the femoral socket to a reduced range of motion which corresponds to acceptable positions of the absorber at full extension. When the knee is placed in full extension and the medio-lateral laxity of the joint is removed by applying varus stress on the knee, the absorber is in a proper position. The tibial base 54 can then be fixed to the anteriomedial surface of the tibia by initially stabilizing with K-wires followed by screw fixation in a manner similar to that used to secure the femoral base 52. In one embodiment, an additional temporary tibial collar may also be used to limit the available range of motion of the tibial articulation during implantation.

The terms "spring" and "absorber" are used throughout the description but these terms are contemplated to include other energy absorbing and compliant structures to accomplish the functions of the invention as described in more detail herein.

While screws are used to fix the femoral and tibial bases 52, 54 to the bone, those skilled in the art will appreciate that any fastening members known or developed in the art may be used to accomplish desired affixation. Although the bases 52, 54 depicted include four to five openings and screws, it is contemplated that other embodiments of the bases may have any number of openings for screws.

Figure 15A:
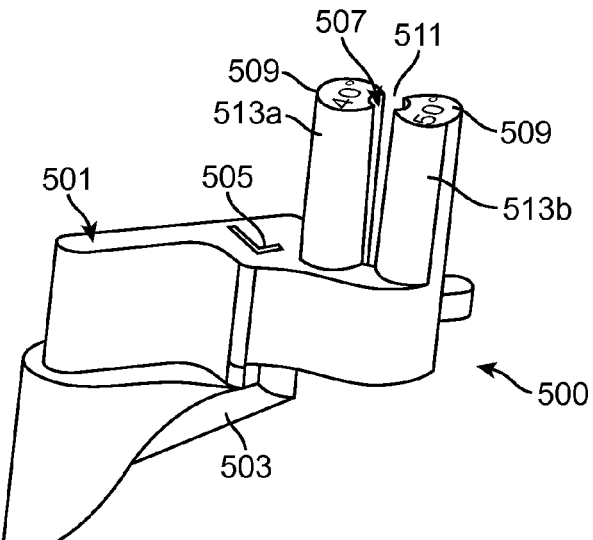
FIGS. 15A-15C are perspective, top and side views of a femoral trial according to an aspect of the present disclosure.
Figure 15B:
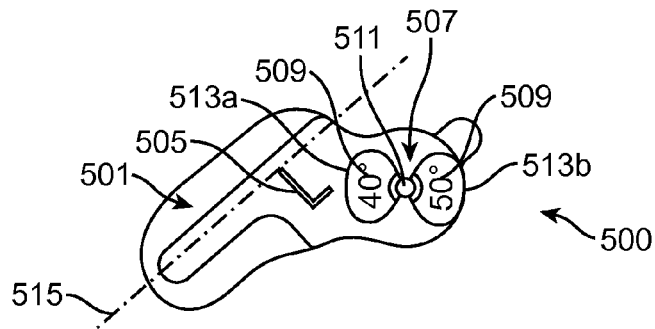
Figure 15C:
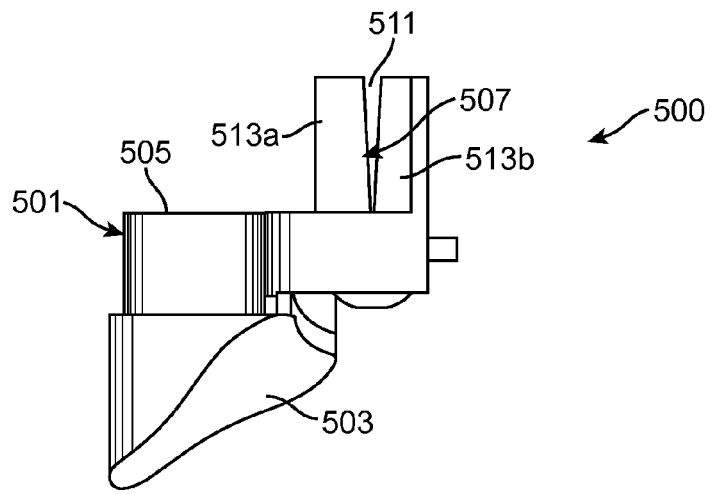

FIGS. 15A-15C show a femoral trial 500 according to an aspect of the present disclosure. The femoral trial 500 functions as a tool for selecting one base from among a plurality of bases having different base geometries for an implant at a joint, such as when the femoral base is provided in two or more versions to accommodate different patient anatomies, such as the 40°, 45°, and 50° base shapes disclosed in U.S. patent application Ser. No. 12/755,335, which is incorporated by reference in its entirety. The trial 500 comprises a tool body 501 having a bone contacting surface 503 with a shape generally corresponding to the shape of bone contacting surfaces of the plurality of bases from which the one base is to be selected. It will be appreciated that the principles associated with the femoral trial are applicable to other joints and joint components, as well.

A bottom surface 503 of the body 501 conforms generally to the shape of the bone to which it is desired to attach a base. A top surface 505 of the body 501 that faces away from the bone may be generally flat or of any other convenient shape for grasping and manipulating the tool.

A guide opening 507 is provided on the tool body 501 and extends through the tool body. The opening 507 is sized to be received over a reference marker, such as a K-wire which has been placed into the bone. The guide opening 507 has indicia 509 adjacent to the opening and corresponding to at least some of the plurality of bases. The guide opening 507 is generally conical, with a wide end 511 of the cone being disposed on a side of the tool body 501 opposite the bottom surface 503 of the tool body intended to face the bone. The indicia 509 are disposed on the tool body 501 at the wide end 511 of the cone of the guide opening 507. The guide opening 507 extends through the tool body 501. In the embodiment of FIGS. 15A-15C, the indecia 509 are located on projecting portions 513 that include two shafts 513a and 513b between which the generally conical opening extends.

During a procedure of placing an joint unloading device, the tool body 501 is positioned on a bone of the joint in a desired alignment with the bone. In the case of the femoral trial 500, an elongated wire reference marker 130 (FIG. 11) is installed in the bone so as to extend generally perpendicular to the tibial plateau and generally parallel to the medial femoral condyle extends through the guide opening. The tool body 501 is positioned so that a long axis 515 (FIG. 15B) of the tool body is aligned parallel to an extended tibial axis and so that the trial base fits on the femur geometry in a fashion so that it is stable on the femur, and the reference marker extends through the guide opening 507.

The reference marker 130 extending through the guide opening 507 will then be disposed in a position relative to the indicia 509 that indicates which base is to be selected from among the plurality of bases. For example, the embodiment of FIGS. 15A-15C is intended to facilitate selection of one of the 40°, 45°, and 50° base shapes disclosed in U.S. patent application Ser. No. 12/755,335. In the example of FIG. 15B, the indicia 509 is in the form of markings that read "40°" and "50°". If the reference marker 130 is centered in the cone of the guide opening 507 and not touching either side, then a 45° base is indicated. If the reference marker 130 touches the side of the cone marked with the "40°" indicia 509, then a 40° base is indicated. If the reference marker 130 touches the side of the cone marked with the "50°" indicia 509, then a 50° base is indicated.

Figure 16A:
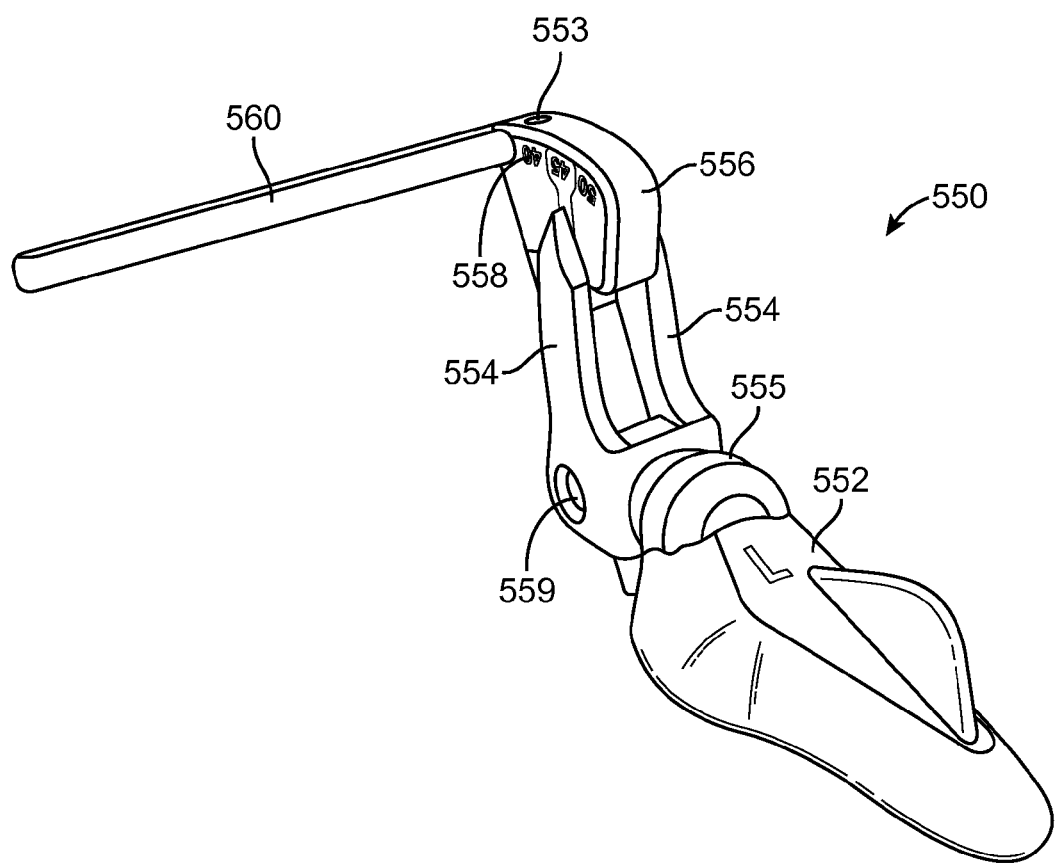
FIGS. 16A-16C are perspective, front and back views of an alternative approach to a femoral trial base.
Figure 16B:
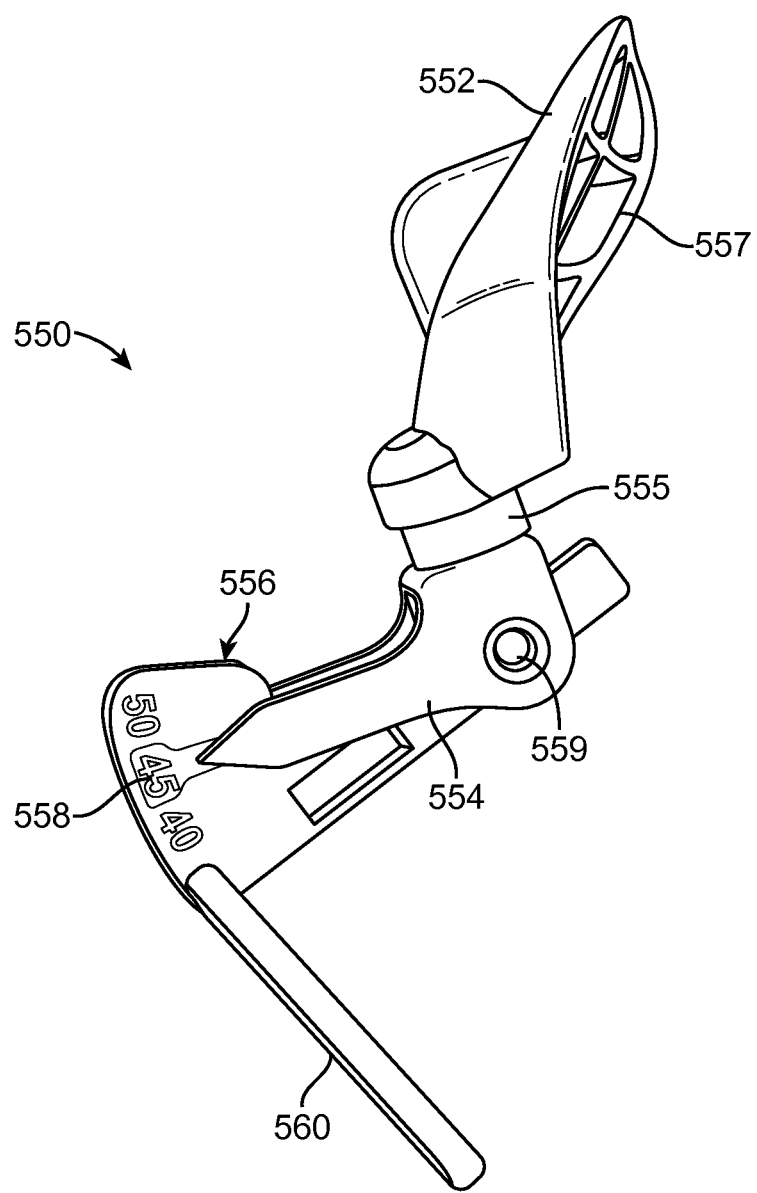
Figure 16C:
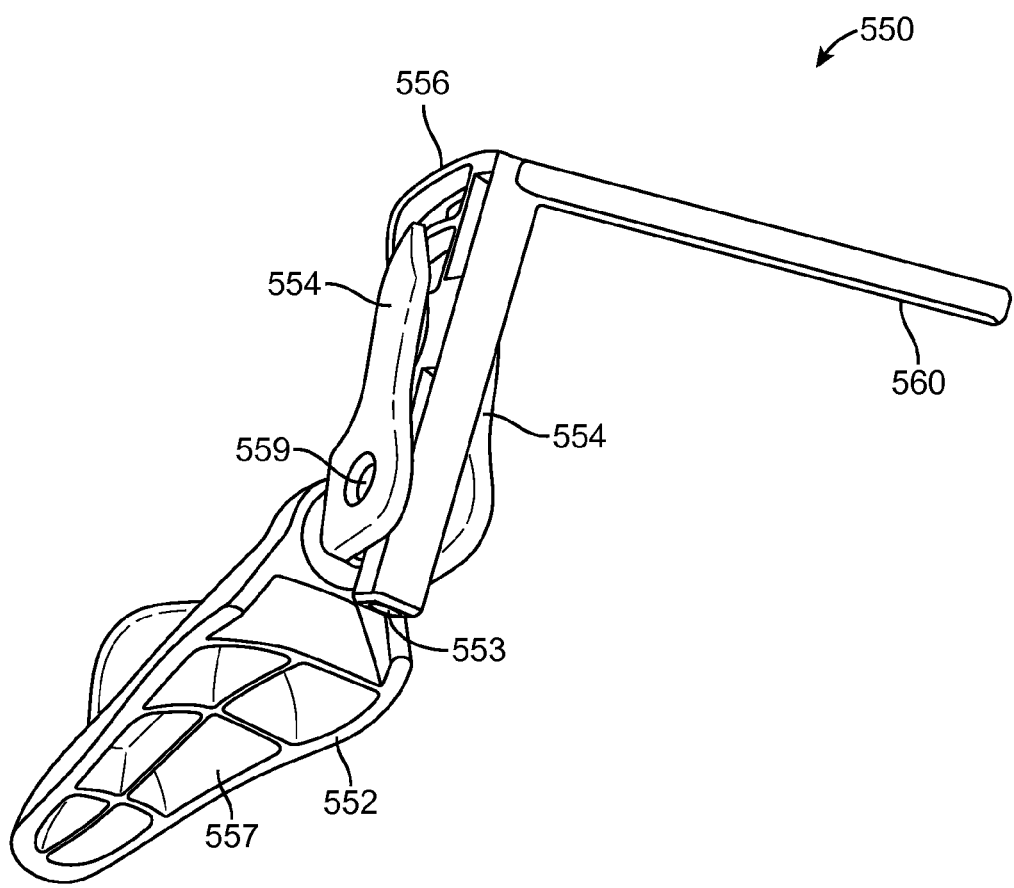

With reference now to FIGS. 16A-C, an alternative femoral trial assembly 550 is presented. The femoral trial assembly 550 includes a trial base 552, which is rotatably connected to both a pointer 554 and an indicia and indicator arm structure 556. As with the previous approach, the trial base portion 552 has a bone contacting surface 557 having a shape generally corresponding to the shape of bone to which the base is to be attached. The indicia portion 558 of the indicator arm structure 556 can include angular markings such as the 40, 45 and 50 degree markings shown, which correspond to various contours for a femoral base. The indicator arm portion 560 is an elongate member that extends away from the indicia portion 558. The pointer 554 overlays the indicia portion 558 and is employed to select the best contour for the femoral base. The indicator arm structure 556 is rotatable with respect to the trial base 552 by a first pivot joint. A second pivot joint 559 allows the indicator arm portion 560 and connected indicia portion 558 to pivot with respect to the pointer 554. Together the first and second pivot joints 555, 559 allow rotation of the indicator arm 560 in two dimensions with respect to the trial base 552 to accommodate a variety of femur configurations. A through hole 553 through the indicator arm structure 556 is provided so that the femoral trial assembly can be received over the femoral reference marker 130.

Figure 16D:
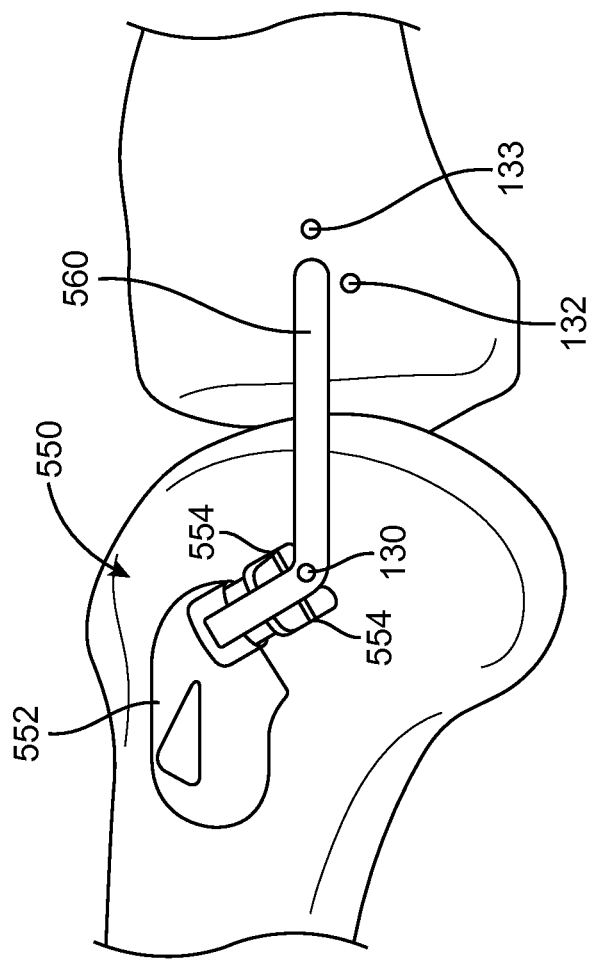
FIG. 16D is a side view, depicting use of the femoral trial base of FIGS. 16A-C.

In use to select a femoral base (See FIG. 16D), the periostium overlaying a femur can be removed or lifted so that the trial base 552 of the trial base assembly 550 can contact bone. The assembly 550 is positioned over or about a femoral reference marker 130. The indicator arm portion 560 is then aligned with the second tibial reference marker 133 and the pointer 554 will identify the correct femoral base contour, for example as 40, 45 or 50 degrees to be selected.

Figure 17B:
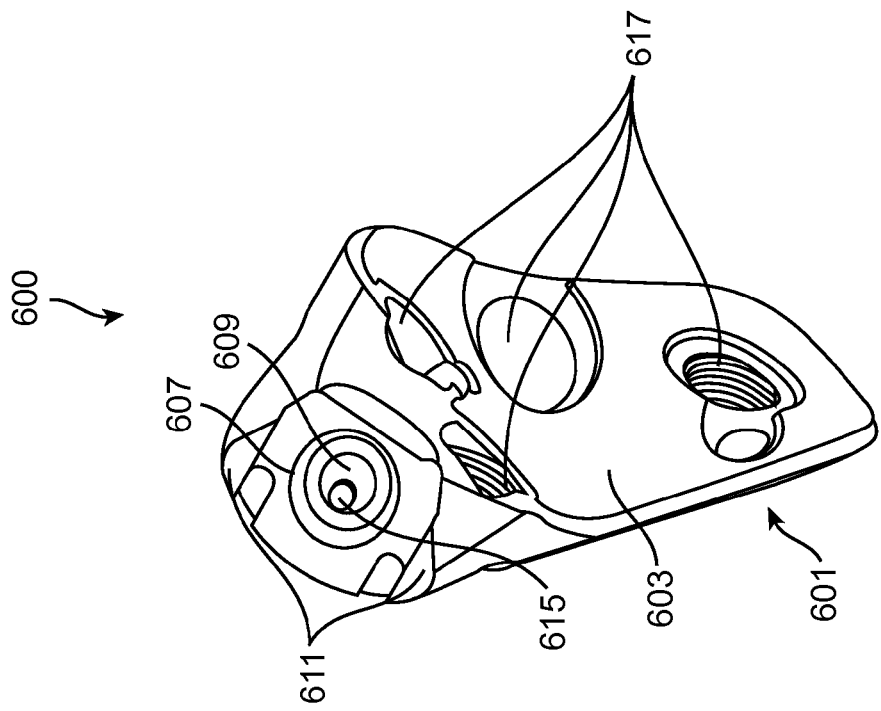
FIGS. 17A-17B are top and perspective views of a base for forming part of a system for placing an joint unloading device at a joint according to an aspect of the present disclosure.
Figure 17A:
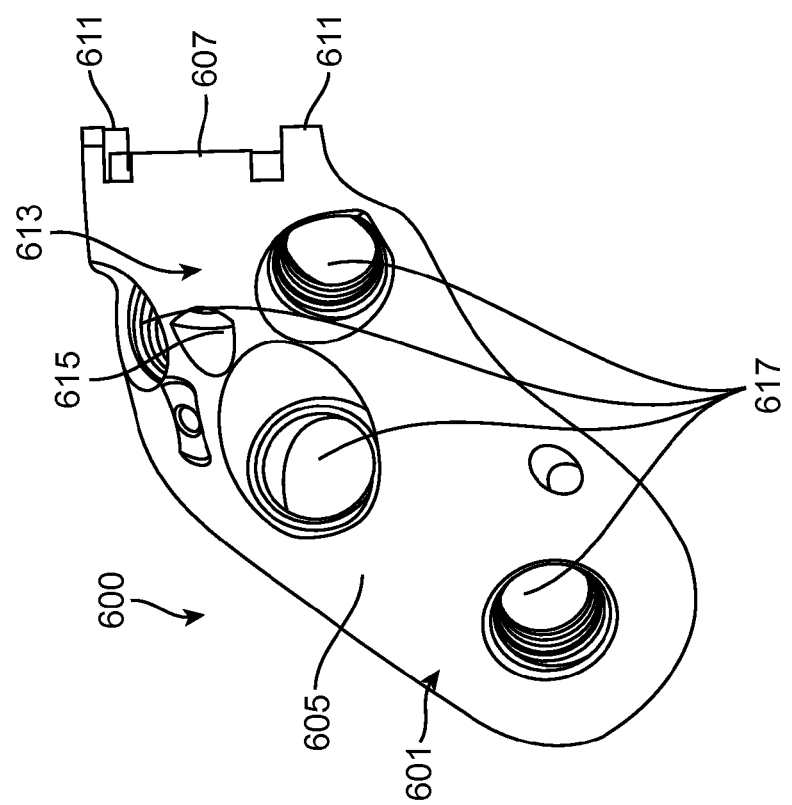
Figure 18A:
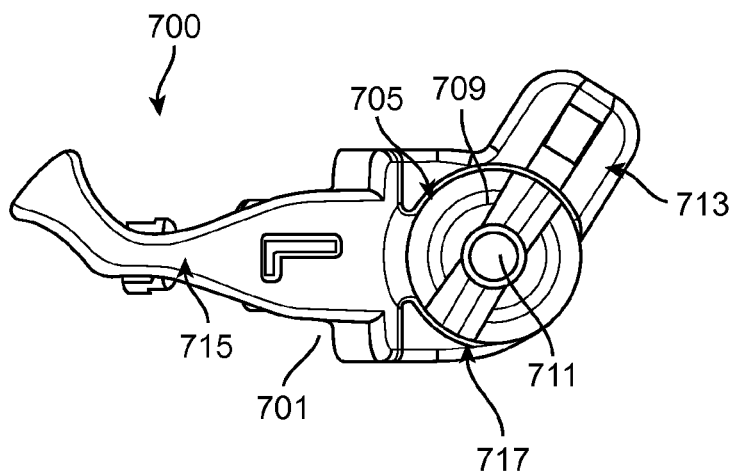
FIGS. 18A-18B are top and perspective views of a placement guide for forming part of a system for placing an joint unloading device at a joint according to an aspect of the present disclosure.
Figures 18B, 19:
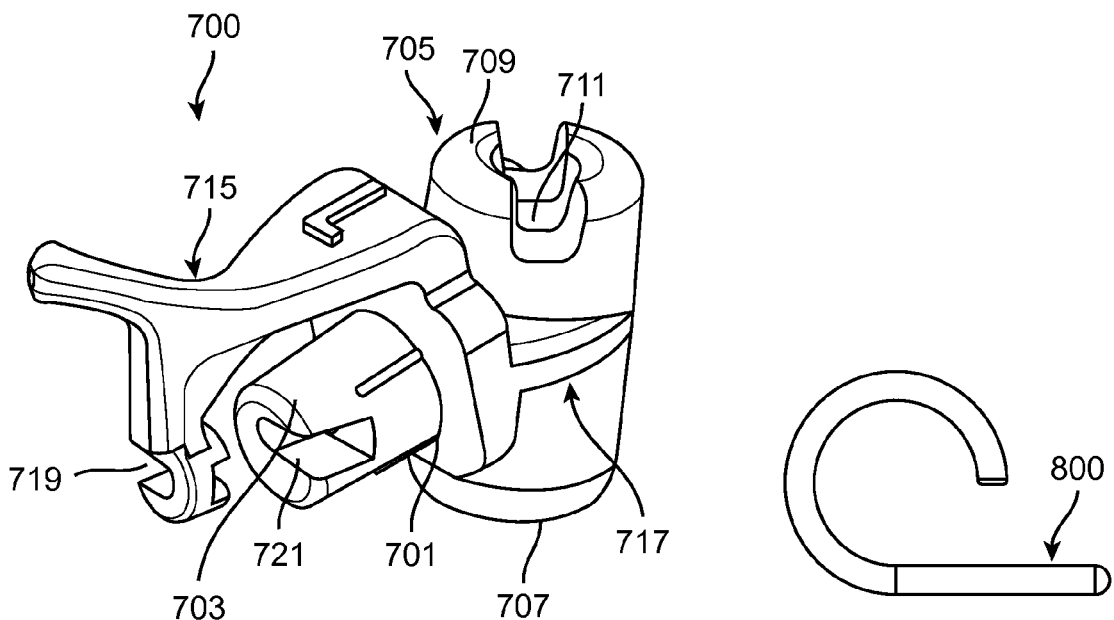
FIG. 19 is a side view of a locking pin forming part of a system for placing an joint unloading device at a joint according to an aspect of the present disclosure.
Figure 20A:
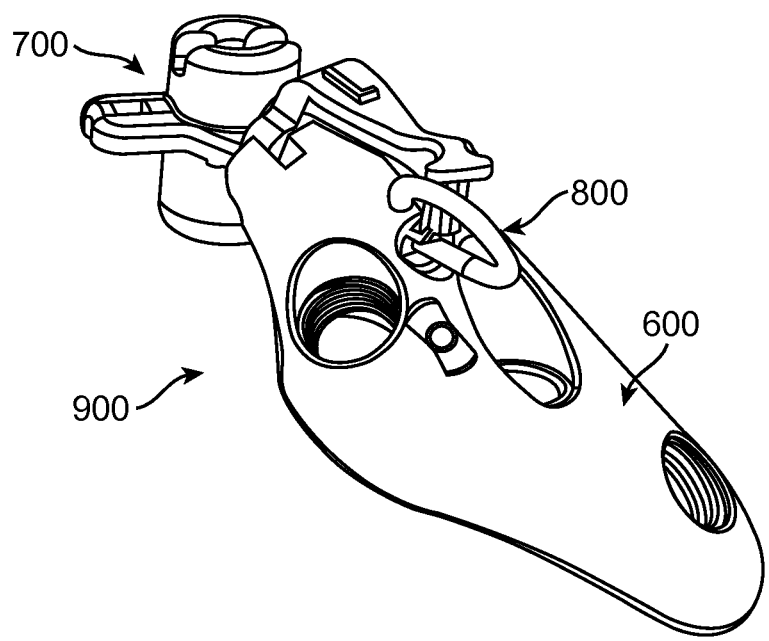
FIGS. 20A-20B are perspective and top views of a system for placing an joint unloading device at a joint according to an aspect of the present disclosure.
Figure 20B:
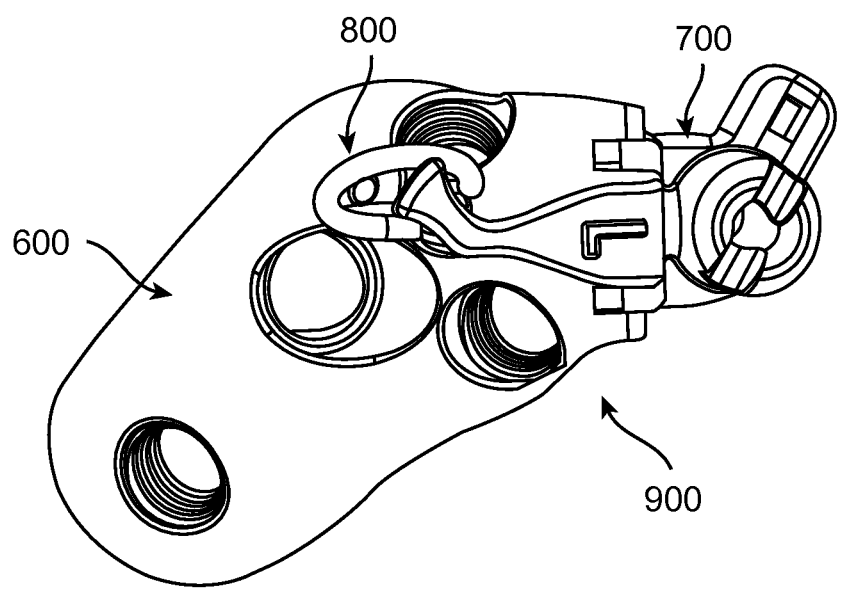

FIGS. 17A-17B show a base 600, FIGS. 18A-18B show a placement guide 700, FIG. 16 shows a locking pin 800 of a system 900, shown in FIGS. 20A-20B, for placing an joint unloading device at a joint, such as a knee joint. The system 900 is designed for use in placing a femoral base of an joint unloading device on a patient's femur, however, it will be appreciated that the principles associated with the system are applicable to other joints and joint components, as well. The system 900 is particularly suited for use in connection with placement of a femoral base of the type that is designed to be placed with an end of the base offset from the bone surface in order to accommodate an articulating portion of the implant in manner disclosed in U.S. patent application Ser. No. 12/755,335, which is incorporated by reference.

The base 600, shown by itself in FIGS. 17A-17B, is configured to be secured to the bone adjacent the joint and has a body 601 including an inner surface 603 facing the bone and conforming generally the shape of the bone, and an outer surface 605 facing away from the bone. The body 601 further includes a first placement guide mounting surface 607 and a first connector component 609.

The placement guide 700, shown by itself in FIGS. 18A-18B, can be formed of, e.g., molded plastic, and includes a second placement guide mounting surface 701, a second connector component 703 adapted to mate with the first connector component 609, and an offset member 705. The placement guide 700 is attachable to the base 600 in an attached position, seen in FIGS. 20A-20B, such that the first and second placement guide mounting surfaces 607 and 701 abut when the first and second connector components 609 and 703 mate. The placement guide 700 is designed to be removable from the base 600 after the base has been secured to the bone so that socket components (not shown in FIGS. 17A-20B) can be attached to the base. After the sockets are attached to the base, an absorber (not shown in FIGS. 17A-20B) having balls for being received in the sockets to form ball and socket joints can be attached to the base on the first placement guide mounting surface 607.

The offset member 705 has a first and a second end 707 and 709. The first end of the offset member 705 is configured to contact the bone when the placement guide 700 is in the attached position and the base 600 is in a position at which it is to be secured to the bone. The offset member 705 further comprises a longitudinal opening 711 and is configured such that a reference marker 130 (FIG. 11) fixed to the bone is adapted to extend through the longitudinal opening when the placement guide 700 is in the attached position and the base 600 is in a position at which it is to be secured to the bone. The reference marker 130 is typically in the form of a wire installed in the bone so as to extend generally perpendicular to the tibial plateau and generally parallel to the medial femoral condyle.

The placement guide 700 may be designed to be attachable to the base 600 in only one attached position. For example, the placement guide 700 may be shaped so that it fits between arms 611 extending from the first placement guide mounting surface 607 that prevent rotation of the placement guide relative to the base 600.

The placement guide 700 further comprises an elongate member 713 having a proximal guide hole (not shown) similar to the proximal guide hole 310 discussed in connection with the embodiment shown in FIGS. 9A-11. The elongate member 713 extends from the guide 700 in a direction towards an opposite bone of the joint and is thus configured for facilitating orientation of the base on the bone when the placement guide 700 is in the attached position and the base 600 is in a position at which it is to be secured to the bone.

The placement guide 700 further includes a locking arm 715 adapted to engage with the base 600 for locking the placement guide in the attached position. The locking arm 715 extends from the main body 717 of the placement guide 700 in an opposite direction relative to the second placement guide mounting surface 701 from the direction of the location of the offset member 705. The locking arm 715 extends around an engagement portion 613 of the base 600 and, while in this locking position, prevents removal of the placement guide 700 from the base. The locking arms 715 is flexible or breakable so that it can be moved from locking position and removal of the placement guide 700 from the base 600 is possible. A removable pin 800 (shown by itself in FIG. 16) engages the locking arm 715 to prevent unlocking of the placement guide 700 from the attached position and extends through openings 719 and 721 in the locking arm and the second connector component 703 and through an opening 615 in the engagement portion 613 of the base.

The system 900 is used to position the base 600 for an implant at a joint by inserting a first reference marker 130 into a first bone of the joint so that one end of the first reference marker is inserted into the bone and the other end of the first reference marker is free. The system 900 in the form of a preassembled combination of a base 600 and a placement guide 700 is positioned on the bone of the joint so that the first reference marker 130 extends through the longitudinal opening 711 in the offset 705, which functions as a first guide hole. A second elongated reference marker such as a wire (not shown) is extended through the proximal guide hole in the elongate member 713 and into the bone of the joint while orienting the system 900 comprising the base 600 and placement guide 700 combination, together with the second reference marker, so that, when the second reference marker is inserted into the bone, the second reference marker extends in a predetermined relation to the first bone and a second bone of the joint. As described in connection with the attachment of the base 52 in FIG. 11, the second reference marker may be a guide wire that extends generally perpendicular to the tibial plateau and generally parallel to the medial femoral condyle. After securing the base 600 to the bone via bone screws through bone screw holes 617, the placement guide 700 is detached from the base 600 by removing the pin 800 and moving the locking arm 715 from the locking position to an unlocked position.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims. In that regard, various features from certain of the disclosed embodiments can be incorporated into other of the disclosed embodiments to provide desired structure.

We claim:

1. A method of implanting a device at a knee joint, the method comprising:
   inserting a first reference marker into a first bone of the joint;
   inserting a second reference marker into a second bone of the joint;
   connecting the first and second reference markers to a verification tool;
   moving the joint through a predetermined range of motion and utilizing the verification tool to determine whether the first and second reference markers move in a desired kinematic pattern with respect to one another throughout the predetermined range of motion;
   aligning the first and second bones and placing an alignment guide across the joint;
   using the alignment guide to properly position the device, including aligning an indicator rod of the alignment guide to be parallel with a tibia and inserting said reference markers through the alignment guide;
   relocating one of the reference markers if the desired kinematic pattern is not achieved;
   removing the first and second reference markers; and
   implanting the device across the joint.

2. The method of claim 1, wherein the device is an joint unloading device.

3. The method of claim 1, wherein the desired kinematic pattern includes motion of the first and second reference markers away from one another as the joint is moved through the predetermined range of motion from extension to flexion.

4. The method of claim 1, wherein the first and second markers comprise elongated members having an end configured for inserting into bone and a free end, and wherein the verification tool has openings for receiving the free ends of the elongated members.

5. The method of claim 1, wherein the verification tool includes an indicator which indicates whether the first and second reference markers move in a desired kinematic pattern.

6. The method of claim 1, wherein the second marker is inserted into the second bone through the opening in the verification tool.

7. The method of claim 1, wherein the verification tool is configured to measure a distance between the first and second reference markers while the joint is moved through the predetermined range of motion.

8. The method of claim 1, wherein the first and second markers are K-wires and are inserted along substantially parallel paths.

9. The method of claim 1, wherein the joint is a knee and the first marker is positioned on a femur relative to a midpoint of Blumensaat's line.

* * * * *